(12) United States Patent
Barzel et al.

(10) Patent No.: US 8,566,040 B2
(45) Date of Patent: Oct. 22, 2013

(54) METHOD FOR SEARCHING FOR HOMING ENDONUCLEASES, THEIR GENES AND THEIR TARGETS

(75) Inventors: Adi Barzel, Moshav Nir-Tzvi (IL); Eyal Privman, Yavne (IL); David Burstein, Tel Aviv (IL); Uri Gophna, Tel Aviv (IL); Martin Kupiec, Tel Aviv (IL); Tal Pupko, Herzelia (IL)

(73) Assignee: Ramot at Tel-Aviv University Ltd, Tel Aviv (IL)

( * ) Notice: Subject to any disclaimer, the term of this patent is extended or adjusted under 35 U.S.C. 154(b) by 52 days.

(21) Appl. No.: 12/867,402

(22) PCT Filed: Feb. 12, 2009

(86) PCT No.: PCT/IL2009/000172
§ 371 (c)(1),
(2), (4) Date: Aug. 12, 2010

(87) PCT Pub. No.: WO2009/101625
PCT Pub. Date: Aug. 20, 2009

(65) Prior Publication Data
US 2010/0317724 A1    Dec. 16, 2010

Related U.S. Application Data

(60) Provisional application No. 61/065,524, filed on Feb. 12, 2008.

(51) Int. Cl.
*G06F 19/00* (2011.01)
*C12Q 1/68* (2006.01)
*C12N 9/16* (2006.01)

(52) U.S. Cl.
USPC .............................. 702/20; 435/6.18; 435/196

(58) Field of Classification Search
None
See application file for complete search history.

(56) References Cited

U.S. PATENT DOCUMENTS

| | | | |
|---|---|---|---|
| 6,528,313 | B1 | 3/2003 | Le Mouellic et al. |
| 6,528,314 | B1 | 3/2003 | Le Mouellic et al. |
| 2004/0137463 | A1 | 7/2004 | Honeycutt et al. |
| 2004/0166561 | A1 | 8/2004 | Poulter et al. |
| 2010/0317724 | A1 | 12/2010 | Barzel et al. |

FOREIGN PATENT DOCUMENTS

| | | |
|---|---|---|
| EP | 419 621 | 10/1990 |
| JP | 3059481 | 7/2000 |
| JP | 3298842 | 7/2002 |
| JP | 3298864 | 7/2002 |

OTHER PUBLICATIONS

Drouin et al. Bochemical characterization of I-Cmoel reveals that this H-N-H homing endonuclease shares functional similarities with H-N-H colicins Nucleic Acids Research vol. 28, pp. 4566-4572 (2000).*
International Search Report for PCT/IL09/00172, mailed on Jul. 15, 2011. 1 page.
Pietrokovski, S., Conserved sequence features of inteins (protein introns) and their use in identifying new inteins and related proteins. Protein Sci, Dec. 1994, vol. 3, pp. 2340-2350.
De Jonckhere et al., Loss of the ORF in the SSUrDNA group I intron of one Naegleria lineage. Nuc. Acids, Res., Sep. 25, 1994, vol. 22, No. 19, pp. 3925-3927.
Burt et al., Homing endonuclease genes: the rise and fall and rise again of a selfish element. Elsevier, Science Direct Curr. Opinion in Genetic & Development, 2004, 14, pp. 609-615.
Stoddard, B.L., Homing endonuclease structure and function. Quarterly Reviews of Biophysics 38, 2006, pp. 49-95.
Paques et al, Meganuclease and DNA Double-Strand Break-Induced Recombination: Perspectives for Gene Therapy. Current Gene Therapy, 2007, 7, pp. 49-66.
Arnould et al., Engineered I-CreI Derivatives Cleaving Sequences from the Human XPC Gene can Induce Highly Efficient Gene Correction in mammalian Cells. J. Mol. Biol. 2007, 371, pp. 49-65.
Smith et al., A combinatorial approach to create artificial homing endonucleases cleaving chosen sequences. Nucleic Acids Research, 2006, vol. 34, No. 22, e149, 12 pgs.
Scalley-Kim et al., Coevolution of a Homing Endonuclease and Its Host Target Sequence. J. Mol. Biol., 2007, 372, pp. 1305-1319.
Kurokawa et al, Adaptation of intronic homing endonuclease for successful horizontal transmission. Febs Journal 272, 2005, pp. 2487-2496.
Stoddard, "Homing endonuclease structure and function," Quarterly Reviews of Biophysics 38, I (2006), pp. 49-95, First Published online Dec. 9, 2005.
http://biochem.uthscsa.edu/~hs_lab/frames/molgen/tutor/blast_databases.html "Databases available for BLAST searching at UTHSCSA", Hardies, Mar. 3, 2005.

\* cited by examiner

*Primary Examiner* — John S Brusca
(74) *Attorney, Agent, or Firm* — Workman Nydegger

(57) ABSTRACT

A computer implemented method for generating nucleotide sequences containing candidate homing endonuclease genes (HEGs). A search is performed in a database stored on a storage medium of nucleotide sequences for amino acid sequences having a subsequence having a homology level with the translation of a subsequence of one or more predetermined HEGs. For each amino acid sequence generated by the search, one or more nucleotide sequences are retrieved encoding the amino acid sequence. The results of this search used in a second search of a database stored on a storage medium to generate the HEG containing sequences.

23 Claims, 4 Drawing Sheets

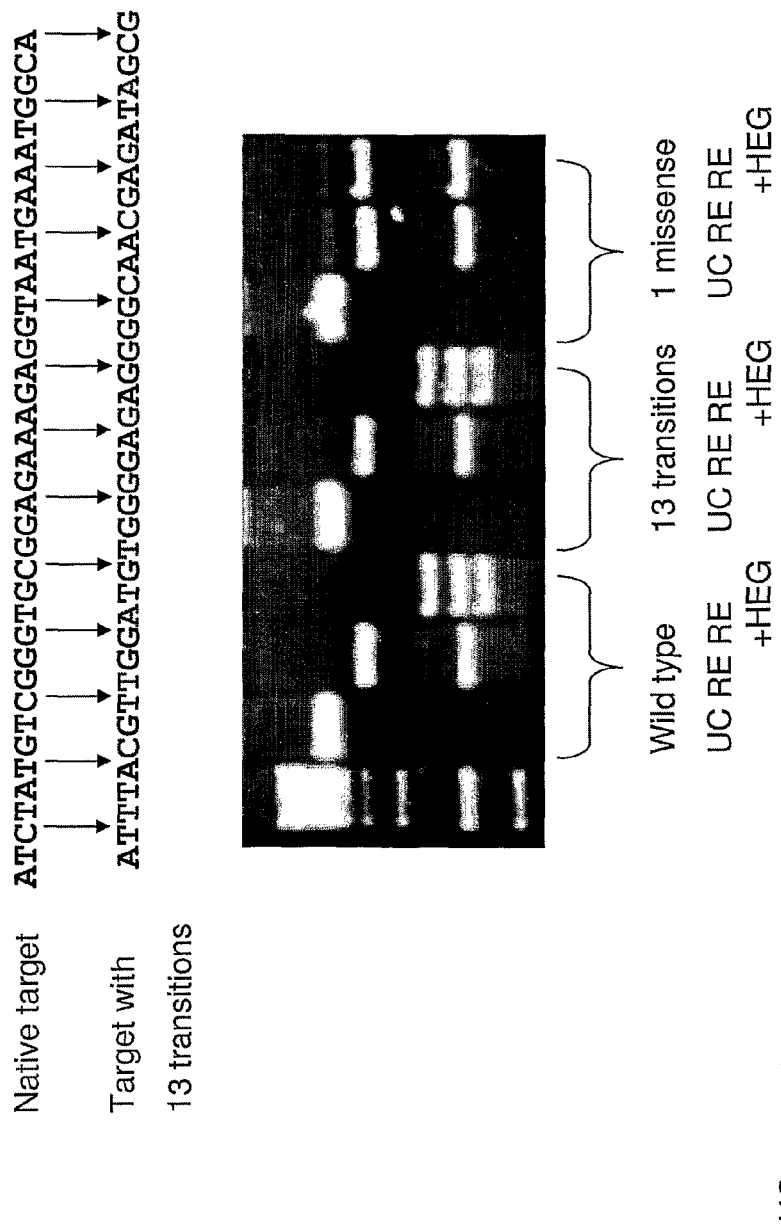
Figure 4a: PI-SceI cleavage assays
Native target  ATCTATGTCGGGTGCCGAGAAAGAGGTAATGAAATGGCA
Target with  ATTTACGTTGGATGTGGGGAGAGGGCAACGAGATAGCG
13 transitions
UC = uncut
RE = cut by the restriction enzyme BspHI
HEG = cut by homing endonuclease gene PI-SceI

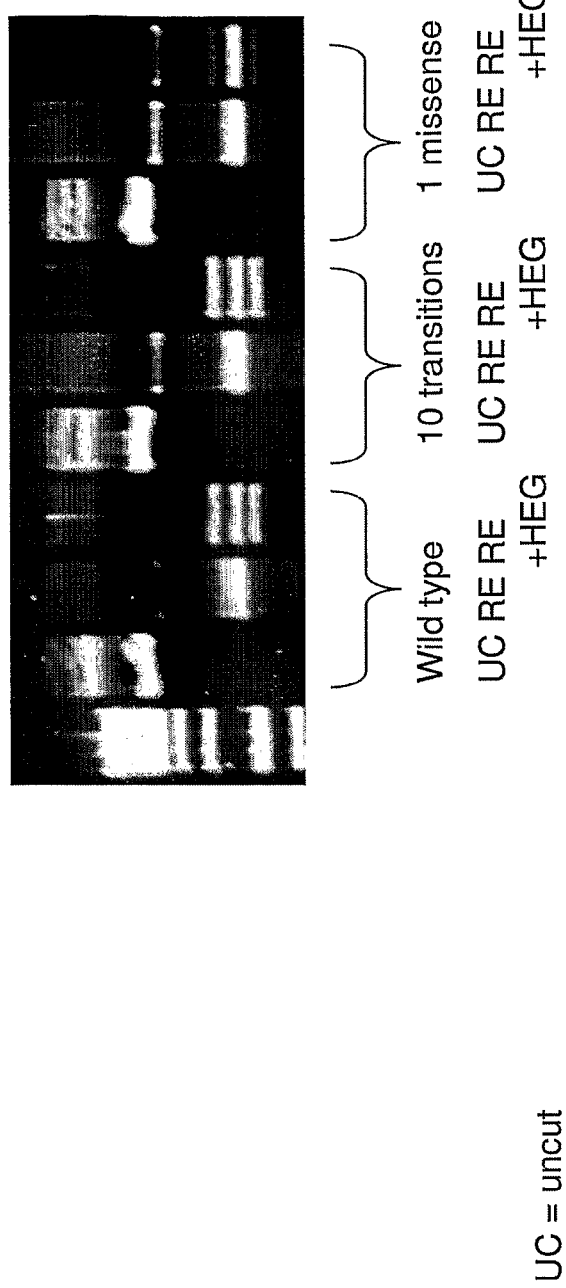
Figure 4b: PI-PspI cleavage assays

METHOD FOR SEARCHING FOR HOMING ENDONUCLEASES, THEIR GENES AND THEIR TARGETS

CROSS-REFERENCE TO RELATED APPLICATIONS

This application is a U.S. Nationalization of PCT Application No. PCT/IL2009/000172 filed 12 Feb. 2009, entitled "METHOD FOR SEARCHING FOR HOMING ENDONUCLEASES, THEIR GENES AND THEIR TARGETS," which claims the benefit of U.S. Provisional Application No. 61/065,524 filed 12 Feb. 2008, entitled "METHOD FOR SEARCHING FOR HOMING ENDONUCLEASES, THEIR GENES AND THEIR TARGETS," the disclosures of each of the foregoing applications are incorporated herein, in their entirety, by this reference.

FIELD OF THE INVENTION

This invention relates to methods for searching in a genetic database.

BACKGROUND OF THE INVENTION

The following prior art references are considered to be relevant for an understanding of the invention:
1. Burt, A. & Koufopanou, V. Homing endonuclease genes: the rise and fall and rise again of a selfish element. *Curr Opin Genet Dev* 14, 609-615 (2004).
2. Stoddard, B. L. Homing endonuclease structure and function. *Q Rev Biophys* 38, 49-95 (2005).
3. Paques, F. & Duchateau, P. Meganucleases and DNA double-strand break-induced recombination: perspectives for gene therapy. *Curr Gene Ther* 7, 49-66 (2007).
4. Arnould, S. et al. Engineered I-CreI derivatives cleaving sequences from the human XPC gene can induce highly efficient gene correction in mammalian cells. *J Mol Biol* 371, 49-65 (2007).
5. Smith, J. et al. A combinatorial approach to create artificial homing endonucleases cleaving chosen sequences. *Nucleic Acids Res* 34, e149 (2006).
6. Scalley-Kim, M., McConnell-Smith, A. & Stoddard, B. L. Coevolution of a homing endonuclease and its host target sequence. *J Mol Biol* 372, 1305-1319 (2007).
7. Kurokawa, S. et al. Adaptation of intronic homing endonuclease for successful horizontal transmission. *Febs J* 272, 2487-2496 (2005).
8. U.S. Pat. Nos. 6,528,313 and 6,528,314, European patent EP 419 621 and Japanese patents JP 3059481, JP 3298842 and JP 3298864.

Gene therapy aims to cure diseases by treating their genetic basis rather than their manifestations. It entails the delivery of corrective genes into affected cells in order to replace, inhibit, correct or compensate for the expression of a disease causing allele. The great promise of gene therapy is to provide a remedy for illnesses that are otherwise difficult to address, such as congenital genetic disorders, neurodegenerative diseases, viral infections and cancer. However, after years of research, two main challenges still stand in the way of wide and successful gene therapy applications. First, the vector carrying the corrective gene must be delivered to the appropriate tissues or cell types and only to them, in order to avoid toxic side effects. Second, when the corrective gene has entered the cell, it must be expressed in a controlled manner, namely, at the correct time, to the appropriate extent and without disturbing the due expression of other important genes. Controlled expression can best be achieved by replacing or correcting the mutated gene at its native location, under the indigenous promoter, where both cis and trans regulators can exert their normal effects. This form of precise correction or replacement is called gene-targeting. In addition to the above medical utilities, gene targeting can also be used for biotechnological enterprises such as crop improvement and for research undertakings such as the engineering of knockout mice strains that allow scientists to model human diseases and test potential remedies.

Transfection of human cells by vectors carrying a corrective gene very rarely results in gene targeting. These rare events are attributed to spontaneous homologous recombination (HR) between the vector-borne gene and the endogenous allele. There are several ways to increase the rate of HR; by far the most effective of which is the induction of a site specific double strand break (DSB). Such DSBs have been shown to raise the frequency of gene targeting by as much as three orders of magnitude. However, induction of a unique DSB is challenging due to the shear size of the human genome (about $3*10^9$ base pairs (bp)). For example, a restriction enzyme with an 8 by long target sequence will cleave the human genome approximately $3*10^9/4^8 \approx 45,776$ times. Such excessive or non-specific cleavage may result in cell death or worse, in genomic instability leading to malignant transformation. There are two major approaches to the challenge of introducing unique DSBs into the human genome. The first approach entails the design of chimeric proteins consisting of a non-specific endonuclease domain linked to a combination of DNA binding domains; the latter are typically zinc finger domains and the chimeras are zinc finger nucleases or ZFNs. ZFNs have been shown capable of inducing gene targeting in human cells. However, much concern has been raised regarding their possible toxicity.

The alternative approach advocates the use and manipulation of naturally occurring site-specific DNAases having long target sequences, namely homing endonuclease genes or HEGs. HEGs are a large and diverse class of site-specific DNAases found in Archaea, Eubacteria and lower eukaryotes, and in their respective viruses. The lengths of HEG target sequences range between 14-40 bp. Furthermore, these targets are not stringently defined. Cleavage is tolerant to some base-pair substitutions along the target sequence. This has raised hopes that at least some HEGs can introduce unique DSBs in desired loci of the human genome. However, only a few hundred HEGs have been annotated to date, and only a few dozen of which have been experimentally characterized. Chances are therefore slim for finding within this limited collection a HEG suitable for gene targeting of a desired gene. One possible way to circumvent this limitation is by attempting to shift the target specificity of a given HEG to make it capable of cleaving a desired sequence (e.g. one that is found within a disease related gene). This has been done with considerable success using a combination of directed enzyme evolution and rational design. Engineered HEGs have been manufactured capable of cleaving XPC (deficient in Xeroderma Pigmentosum), IL2RG (deficient in X-linked SCID—severe combined immunodeficiency), Rag1 (deficient in autosomal recessive SCID) and the tumor suppressor gene p53. Despite its achievements, HEG-engineering is an inherently limited approach; using directed evolution and rational design one can only alter target specificity up to a certain extent. Therefore, for HEG mediated gene targeting to become a common medical practice, the arsenal of target sites must be dramatically extended by the discovery of many more naturally occurring HEGs.

A homing endonuclease (HE) cleaves a long (14-40 bp), rather specific, DNA target sequence. FIG. 1 shows schematically the expression of a HEG, and the activity of a HE. A HEG 2 is found within a self-splicing intron 4 or intein (not shown) within a gene 6. The active HE 8 is produced following splicing of the mRNA transcribed from the gene 6, or splicing of the protein translated from the mRNA. The HE 8 recognizes and cleaves a target sequence 10 in a "vacant allele" 12 of the gene 6 which lacks the intron 4 or the intein. The HE 8 can then promote the insertion of a copy of the intron 4 or the intein into the vacant allele 12 by homologous recombination (homing) or reverse transcription (retro-homing)[1,2]. Thus, the HE target site 10 also marks the insertion site of the intron 4.

HEs have been utilized in gene targeting procedures where the introduction of site-specific double-strand-breaks facilitates gene correction, disruption or insertion at a locus of choice[3]. U.S. Pat. Nos. 6,528,313 and 6,528,314, European patent EP 419 621 and Japanese patents JP 3059481, JP 3298842 and JP 3298864 disclose use of homing endonucleases in gene targeting.

For a HE capable of cleaving only its cognate target, straightforward probabilistic considerations would render HE-mediated gene targeting a virtual impossibility. For example, a 25 by long target sequence would be expected to be found at random every $4^{25} \approx 10^{15}$ bp. It has a one in a million chance of being found anywhere in the human genome, let alone in a medically important gene.

Only a few hundred HEs have been identified, and only a few dozen of them have been characterized experimentally. The chances are small of finding within this limited collection a HE capable of cleaving a selected nucleotide sequence (e.g. a sequence found within a disease related allele of a gene). One possible way to overcome this limitation is by attempting to change the target specificity of a given HE so that the GH can cleave the selected sequence. This has been done using a combination of directed enzyme evolution and rational design. HEs have been engineered capable of cleaving XPC (deficient in Xeroderma Pigmentosum), IL2RG (deficient in X-linked SCID-severe combined immunodeficiency), Rag1 (deficient in autosomal recessive SCID) and the tumor suppressor gene p53. However, HE-engineering is an inherently limited approach in that directed evolution and rational design one can only alter the target specificity to a limited extent.

Burt, and Koufopanou[1] and Stoddard[2] have reported HEs capable of cleaving base-pair sequences differing from their cognate target site by at most a few base pair substitutions[1,2]. Base-pair substitutions at non-conserved positions are, in general, better tolerated by the HE than base pair substitutions at highly conserved positions[6,7]. In particular, HEs are more tolerant of synonymous substitutions than they are of non-synonymous substitutions[6,7].

SUMMARY OF THE INVENTION

In its first aspect the present invention provides a method for searching for candidate HEGs within a nucleotide sequence database. The invention also provides a method for searching for cleavable targets of a HE within a nucleotide sequence database. Searching for cleavable targets of a HE within a nucleotide database may utilize the novel and unexpected finding of HEGs in protein encoding genes capable of cleaving targets differing from their cognate target by as much as all synonymous substitutions. The invention also provides a method for determining genes capable of being cleaved by a HE.

One presently preferred embodiment of the invention comprises the following steps:

1) A search is performed using a HEG dataset as a search query. The HEG dataset consists of one or more known HEGs, and may be formed by combining one or more HEG-datasets into a single dataset. For example, the HEG dataset may be a combination of HEG sequences from any one or more of the following databases: InBase, sequences in the learning sets of relevant HMMs and the NCBI Protein search results for the query: "homing endonuclease". The search may consist of running blast or tblastn on the GENBANK™ databases nt and env_nt (protein query against translated nucleotide), using a permissive e-value, such as 10. The output of this stage is a list of potential HEGs (pHEGs). This search is continued using PSI-BLAST iterations.

2) For a pHEG of nt origin, the DNA sequence of the pHE+1 Kb on each side of the pHEG are determined. For a pHEG of env_nt origin, the DNA sequence of the contig is determined. The DNA sequences that are output at this stage are referred to herein as "hosting genes".

3) For every hosting gene, tblastx is run against nt and env_nt (translated nucleotide query against translated nucleotide database).

4) Hosting genes of pHEGs are sought in the same database used in the search of step 1 having vacant homologues. A vacant homologue of a hosting gene is defined to be a sequence that a) has a homology level above a predetermined threshold to the hosting gene, both upstream and downstream to the pHEG independently; b) bears a deletion of a length above a predetermined threshold such as 900 by with respect to the hosting gene; and c) the deletion encompasses the pHEG in the original hosting gene.

5) For every pHEG whose hosting gene has a vacant homologue, the tblastx hits of the pHEG. i.e. homologues of the homing endonucleases domain, are collected using a stringent e-value.

6) For every pHEG whose hosting gene has a vacant homologue, a phylogenetic tree based on its hits obtained in step 5 is constructed.

7) For every pHEG whose hosting gene has a vacant homologue, a Ka/Ks score is determined based on its phylogeny obtained in stage (7).

8) pHEGs having a Ka/Ka/Ks score above a predetermined threshold are filtered out. The remaining pHEGs are presumed to be exposed to purifying selection and have thus not degenerated. The pHEGs remaining after this filtering step are designated as HEGs.

9) The HEGs are divided into two sets: the HEGs which are in-frame with their hosting gene (intein-HEGs) and those who are not (intron-HEGs). Both sides of the HEG should be checked in order to determine whether or not a HEG is in-frame.

10) For every intron-HEG, on the basis of the step 3 tblastx results, an intron-HEG is defined to be an "intronP-HEG" (intron-HEG within a protein coding gene) if it is similar (stringent e value) to an open reading frame, a hypothetical open reading frame or a truncated reading frame of over 50 amino acids long (from an environmental contig). Otherwise, the intron-HEG is defined to be an "intronR-HEG" (intron-HEG within an RNA gene).

The order of the steps in this method may be changed. For example, the finding of vacant homologues can precede the similarity search (for example, if an all against all BLAST is followed by a search for insertions and deletions that satisfy the above requirements). As another example, the Ka/Ks measurements can precede the search for vacant homologues and so forth.

As noted above, the insertion site of an intron/intein also marks the target site of its respective HE. By comparing a HEG-containing gene to a vacant homologue of the gene, the insertion site of the HEG can be deduced. For the gene search, an amino acid target site of the HE is designated. The amino acid target may be specified by a first predetermined number of amino acid residues 5' to the insertion site and a second predetermined number of amino acids 3' to the insertion site. As the length of the designated amino acid target is increased, the number of genes retrieved in the gene search decreases, but the confidence in the hits increases (the number of false positives decreases and the number of false negatives increases).

In one embodiment the length of the amino acid target may be determined using, the following procedure:
1) For a given intein-HE, designate the target site extending from 5 amino acids and 8 amino acids flanking the intein at its 5' and 3' borders respectively.
2) For every intronP-HE define the target site as follows: a) If the 3' end of the 5' exon is a third position of a codon, define the target site as extending from the 5 amino acids and 8 amino acids flanking the intron at its 5' and 3' borders respectively. b) If the 3' end of the 5' exon is a first position of a codon (the second and third positions of this codon are on the 3' exon), define the target site to extend from the 5 amino acids upstream to that codon, to 7 amino acids downstream to it (on the 3' exon). c) If the 3' end of the 5' exon is a second position of a codon, define the target site to extend from the 4 amino acids upstream to that codon, to 8 amino acids downstream to it (on the 3' exon).
3) Search for targets of the HE using the designated target.

In accordance with this aspect of the invention, a search is conducted in a HE target database using one or more genes of interest as the search query. For example, it may be a BLAST of the database OMIM (the NCBI database of disease related genes) against a HE amino acid target site database, in which disease related genes that can be cleaved by one or more HEs are sought. In the search, it is not necessary to require that the similarity to the OMIM gene be in the native reading frame of the OMIM genes. BLAST hits to frame shift translation of a certain OMIM gene also indicate that this DNA sequence is cleavable by the HE. A hit to the opposite strand of the OMIM gene may be just as useful. A target site in an intron of the OMIM gene may also be useful. Therefore, blastx is preferably used to search for a match between all six possible translations of the unspliced sequence of the OMIM gene against the amino acid sequences of the target site.

The default BLAST search preferably takes into account the chemical nature of the mismatched amino acids in the sequences retrieved by the search. If, for example, both amino acids are hydrophobic the mismatch is assigned a low penalty in comparison to a mismatch between hydrophobic and a hydrophilic amino acids.

When a gene of interest revealed in a search matches a HE target site only approximately, but not exactly, the HE may be slightly modified to increase its specificity towards the gene. As mentioned above, this has been done to prepare HEs capable of cleaving disease related genes such as XPC and RAG1 using a combination of directed enzyme evolution and structure-based rational design. Both of these methods are most efficient when the native target and the desired target are similar at the nucleotide level.

In an embodiment, penalties are assigned using specialized PAM matrices. Unlike the default matrix that gives a higher ranking for the alignment of mismatched amino-acids when these have similar chemistry (similar hydrophobicity, pKa, etc), the specialized matrix gives higher ranking to the alignment of mismatched amino acids whose codons are more similar on the average at the nucleotide level. For example: Histidine is basic and glutamine is an amide, but their codons differ by only one nucleotide. Therefore, it should be relatively easy to make a HEG bind a histidine codon where its native target site encodes glutamine. The specialized matrix render histidine and glutamine "similar" while asparagine and glutamine (both amides) would be regarded as more distant because there are two amino acid differences between their codons.

If two homologous HEGs X and Y reside within homologous hosting genes, then the HE X may be able to cleave the target of HE Y and vice versa, even if the targets differ by non-synonymous substitutions, and even if the hosting gene is RNA. The closer X and Y are to each other, the greater the chance of such cross-cleavage is expected to be. Thus, in a preferred embodiment, each possible nucleotide at each position along the target of each given HE is ranked. If a position is conserved in all the targets of homologous HEs the conserved nucleotide will receive the ranking 1 and all other nucleotides will receive the ranking 0. Conversely, if, for example, HEG X has the nucleotide T at position P of its target, and if some of X's homologues have the nucleotide G at position P, then T will still get the ranking 1 but G will also get a positive ranking which is proportionate to the number of homologous HEGs that have G in the P position at their targets and also proportionate to the evolutionary distance of these HEGs from X. Finally, HomeBase2 must also incorporate the notion of confidence value for each claim made.

In another embodiment, the two approaches are combined. For example the targets of a HE whose gene resides within a protein coding gene are first found and then targets of HEs whose gene resides in RNA genes are determined. Alternatively, the targets of HEGs in protein coding genes can be defined as a profile of amino acids where each amino acid at each position is ranked.

In another preferred embodiment, structural information on a HE is utilized. HEs are divided into structural families (LAGLIDADG, HNH, etc. . . . ) and sub-families (homodimeric LAGLIDADG, monomeric LAGLIDADG, etc. . . . ). Representatives of each family have been studied in great detail. In accordance with this embodiment, if HE X of structural family F was found to cleave a target spanning 11 amino acids, three on the 5' side and 8 on the 3' side of the insertion site, this target configuration is attributed to all members of family F. In yet another example, if HE Y belongs to the subfamily of homodimeric LAGLIDADGs, which are known to cleave palindromes, the target-profile of Y will favor palindromes.

If the DNA binding domains of two HEs share structural similarity, this can be taken to suggest that they bind similar targets, or at the very least, that they bind their targets in a similar manner. For example, if one of the two is known to be oblivious of the content of position P along its target site, the other HEG is also assumed to be oblivious of that position.

Genomic databases include fully and partially sequenced genomes of organisms ranging from cultured bacteria to man. In contrast, metagenomic databases consist of short DNA sequences from uncultured organisms. The number of cultured organisms is limited. However, the metagenomic data are defective in several ways. Most importantly, the sequences in the metagenomic databases (known as "contigs") are short. Many putative HEGs of metagenomic origin would be excluded from the HEG database used in the invention because they are found truncated on a short contig. Even when the entire open reading frame is present on a single contig, it is sometimes not enough. The same contig must also encode for a sufficiently long segment of the hosting gene as to allow for the detection of a vacant homologue. This limitation can be addressed in several levels. First, a library of longer metagenomic sequences can be constructed ad hoc (for example by cloning on cosmids) and then screened for HEGs (for example by degenerated PCR). Alternatively, the invention can be implemented on truncated HEGs. PCR primers can be made to fit the predicted target sequences and then used to amplify the full HEG from an environmental sample. Finally, existing metagenomic databases are also limited in that they under-represent both viruses and fungi. The latter two groups are known to be rich in HEGs. A specialized metagenomic survey can be conducted that better represents these groups.

Thus, in one of its aspects, the invention provides a computer implemented method for identifying a first set of nucleotide sequences containing candidate homing endonuclease genes (HEGs). In accordance with this aspect, a first search is performed in the six frame translation of a first nucleotide sequence database for amino acid sequences having subsequences homologous to the translation of a subsequence of a predetermined HEG. For each amino acid sequence generated by the search, the nucleotide sequences encoding the amino acid sequence are retrieved to generate a first set of search results.

A second search is then performed in the six frame translation of a second nucleotide sequence database for amino acid sequences having a subsequence homologous to a subsequence of a translation of a sequence belonging to the first set of search results. For every amino acid sequence generated by the second search, nucleotide sequences encoding for the amino acid sequence are retrieved, to generate a second set of search results. The first set of sequences containing candidate HEGs is then generated in a process involving the first and second search results.

In one embodiment, the first set of sequences containing candidate HEGs is generated, where a sequence in the first set of sequences containing candidate HEGs is a sequence in the first set of search results having at least one protein coding vacant homolog. FIG. 2 shows the structure of a protein coding vacant homolog 20 of a HE 19. As used herein the term "protein coding vacant homolog" refers to a nucleotide sequence 20 belonging to the second set of search results having:

(a) a subsequence 22 whose translation is homologous to the translation of a subsequence 24 of a sequence 21 from the first set of search results;

(b) a subsequence 26 downstream and adjacent to the subsequence 22 whose translation is homologous to the translation of a subsequence 28 of the sequence from the first set of search results;

Where:

(a) the subsequences 24 and 28 are separated by a subsequence 30, whose translation is homologous to an interval 33 of the HE.

(b) the subsequence 30 is longer than a predetermined length.

(c) the translation of subsequence 22 is continuous and longer than a predetermined length;

(d) the translation of subsequence 24 is continuous and longer than a predetermined length;

(e) the translation of subsequence 26 is continuous and longer than a predetermined length;

(f) the translation of subsequence 28 is continuous and longer than a predetermined length;

The method may further comprise identifying a first set of candidate HEGs, having two subsets. The first subset comprises inteins, namely subsequences 30 of one or more of the sequences belonging to the first set of sequences containing candidate HEGs for each sequence in the first set of sequences for which the subsequence 30 is in the same reading frame as that of the subsequences 24 and 28. The second subset comprises HEGs residing in introns, namely sequences of the first set of candidate HEGs comprising sequences each of which is a subsequence 29 of the sequence 30, wherein the subsequence 30 is not in the reading frame of either one or both of the subsequences 24 and 28 of the sequence, and the subsequence 29 is an open reading frame beginning with a start codon and ending with a stop codon, and is longer than a predetermined length.

Thus, in its first aspect, the invention provides a computer implemented method for generating a first set of hosting sequences, the hosting sequences being nucleotide sequences containing candidate homing endonuclease genes (HEGs) or a second set of hosting sequences, comprising:

(a) performing a first search in the six frame translation of a first database stored on a storage medium, the first database being comprised of nucleotide sequences, for amino acid sequences having at least one subsequence having at least a predetermined homology level with the translation of at least one subsequence of one or more predetermined HEGs; and, for each amino acid sequence generated by the search, retrieving one or more nucleotide sequences from the first database encoding the amino acid sequence, to generate a first set of search results;

(b) performing a search selected from:

(i) a second search in the six frame translation of a second database stored on a storage medium, the second database being comprised of nucleotide sequences, for amino acid sequences having at least one subsequence having at least a predetermined homology level with at least one subsequence of at least one of the six frame translations of at least one sequence belonging to the first set of search results; and, for every amino acid sequence generated by the second search, retrieving one or more nucleotide sequences encoding for the amino acid sequence, to generate a second set of search results; and (ii) a third search in a third database stored on a storage medium of nucleotide sequences for sequences having at least one subsequence having at least a predetermined homology level with at least one subsequence of a sequence belonging to the first set of search results, to generate a third set of search results; and (c) generating the first set of hosting sequences in a process involving identifying in the second set of search results one or more protein coding vacant homologs for each of one or more sequences of the first set of search results, or generating the second set of hosting sequences in a process involving identifying in the third set of search results one or more RNA coding vacant homologs for each of one or more sequences of the first set of search results, wherein a protein coding vacant homolog being a nucleotide sequence belonging to the second set of search results for which at least one of the six frame translations of the sequence from the second set of search results includes a first interval having at least a predetermined homology level with a second interval of one of the six frame translations of the sequence belonging to the first set of search results, and the translation of the sequence from the second set of search results further having a third interval C' and adjacent to the first interval, the third interval having at least a predetermined homology level with a fourth interval in one of the six frame translations of the sequence belonging to the first set of search results, the nucleotide sequences encoding the second and forth intervals being separated by a fifth interval, the fifth interval containing a subinterval, the translation of the subinterval having at least a predetermined homology level with a sixth interval of the translation of one or more predetermined HEGs, and the fifth interval is longer than a predetermined threshold, and (d) displaying the results on a display device; and wherein an RNA coding vacant homolog being a sequence belonging to the fourth set of search results including a first interval having at least a predetermined homology level with a second interval of the sequence belonging to the third set of search results, and the sequence from the fourth set of search results further having a third interval downstream and adjacent to the first interval having at least a predetermined homology level with a fourth interval in the sequence belonging to the third set of search results, the second and forth intervals being separated by a fifth interval, the fifth interval containing a subinterval, the translation of the subinterval having at least a predetermined homology level with a sixth interval of the translation of one or more predetermined HEGs, and the fifth interval is longer than a predetermined threshold.

The method may comprise identifying in the second set search results one or more protein coding vacant homologs for each of one or more sequences of the first set of search results, and further comprising, filtering from the first set of sequences containing candidate HEGs those sequences not satisfying at least one of the following conditions:

i) The translations of both the first and the second intervals according to the homologous reading frames are continuous and longer than a predetermined threshold; and ii) The translations of both the third and the fourth intervals according to the homologous reading frames are continuous and longer than a predetermined threshold.

The method may comprise further generating from the first set of hosting sequences, a first set of candidate HEGs comprising candidate HEGs residing in inteins.

The method may comprise further generating from the first set of hosting sequences, generating a second set of candidate HEGs comprising candidate HEGs residing in introns of protein coding genes.

In one embodiment of the invention, the first set of candidate HEGs comprises the fifth interval of one or more of the nucleotide sequences belonging to the first set of hosting sequences for each nucleotide sequence in the first set of hosting sequences for which the fifth interval is in the same open reading frame as the nucleotide sequences encoding the second and fourth intervals of the nucleotide sequence in the first set of hosting sequences.

In one embodiment of the invention, the second set comprises one or more nucleotide sequences each of which is a subsequence of a fifth interval of a nucleotide sequence belonging to the first set of hosting sequences, wherein the fifth interval is not in the reading frame of either one or both of the nucleotide sequences encoding the second and fourth intervals of the nucleotide sequence in the first set of hosting sequences, and the subsequence is an open reading frame beginning with a start codon and ending with a stop codon, and the subsequence being longer than a predetermined threshold.

The method of the invention may comprise identifying a third set of candidate HEGs residing in introns of RNA genes, the third set of candidate HEGs comprising one or more nucleotide sequences, each sequence being a subsequence of a fifth interval of a nucleotide sequence belonging to the second set of hosting sequences, wherein the fifth interval is not in the reading frame of either one or both of the nucleotide sequences encoding the second and fourth intervals of the nucleotide sequence belonging to the second set of hosting sequences, and the subsequence is an open reading frame beginning with a start codon and ending with a stop codon, and the subsequence being longer than a predetermined threshold.

The method of the invention may comprise filtering the first set of hosting sequences or second set of hosting sequences, comprising:

(a) for each of one or more nucleotide sequences belonging to the first set of hosting sequences, calculating a Ka\Ks ratio based upon multiple alignment and phylogenetic reconstruction of a set of amino acid sequences, wherein the calculating comprises:
  i) the homing endonuclease (HE) encoded by the candidate HEG of the hosting sequence, and
  ii) a set of intervals found within the translation of nucleotide sequences in the second set of search results, each interval having a homology level above a predetermined homology level with the translation of at least a subsequence of the fifth interval of the nucleotide sequence belonging to the first set of hosting sequences; and
  iii) filtering out from the first set of hosting sequences nucleotide sequences containing degenerate candidate HEGs, a nucleotide sequence containing a degenerate candidate HEG having Ka/Ks ratio above a predetermined level; or (b) for each of one or more sequences belonging to the second set of hosting sequences, calculating a Ka\Ks ratio based upon multiple alignment and phylogenetic reconstruction of a set of amino acid sequences comprising:
  i) the candidate HE encoded by the candidate HEG of the hosting sequence, and
  ii) a set of intervals found within the translation of nucleotide sequences in the second set of search results or in the third set of search results, each interval having a homology level above a predetermined threshold with the translation of at least a subsequence of the fifth interval of the nucleotide sequence belonging to the second set of hosting sequences; and
  iii) filtering out from the second set of hosting sequences, nucleotide sequences containing degenerate candidate HEGs, a nucleotide sequence containing a degenerate candidate HEG having Ka/Ks ratio above a predetermined level, The method of the invention may comprise determining a nucleotide sequence containing a cognate target of a candidate homing endonuclease (HE) encoded by a candidate HEG, the nucleotide sequence being a union of a nucleotide sequence containing a 5' half target and a nucleotide sequence containing a 3' half target, the nucleotide sequence containing the 5' half target being a nucleotide sequence of predetermined length upstream and adjacent to the 5' end of the fifth interval of the hosting sequence, and the nucleotide sequence containing the 3' half target being a nucleotide sequence of predetermined length downstream and adjacent to a 3' end of the fifth interval of the of the hosting sequence.

The method invention may further comprise:
(a) generating a fourth database stored on a storage medium of elements, each element being a pair of the fourth database and comprised of a candidate HE and the amino acid target of the HE of the pair of the fourth database, the candidate HE being encoded by a candidate HEG obtained by the method according to the invention, and the amino acid target being an amino acid sequence encoded by a nucleotide sequence containing a cognate target of the candidate HE obtained by the method according to the invention, wherein, the translation of the sequence containing the cognate target is in the reading frame defining the homology between the translation of the first interval and the translation of the second interval; or
(b) generating a fifth database stored on a storage medium of elements, each element being a pair of the fifth data base and comprised of a candidate HE and the target of the HE of the pair of the fifth database, the candidate HE being encoded by a candidate HEG obtained by the method according to the invention, and the target of the HE being a sequence containing the cognate target obtained by the method according to the invention.

The invention may further comprise identifying in a sixth database stored on a storage medium of nucleotide sequences or a seventh database stored on a storage medium of nucleotide sequences, candidate nucleotide targets of one or more candidates HEs, the method comprising:
(a) performing a search for matches between the fourth database and the six frame translation of a sixth database stored on a storage medium, a match being a pair comprised of a first element being the amino acid target of a pair in the fourth database and a second element belonging to the six frame translation of the sixth database, the first element having a homology level above a predetermined homology level with the second element; and for each match generated by the search retrieving the nucleotide sequence encoding the second element of the match, to obtain candidate nucleotide targets of one or more candidates HEs; or
(b) performing a search for matches between the fifth database and a seventh database stored on a storage medium, a match being a pair of the seventh database and comprised of a first element being the target of a pair in the fifth database and a second element belonging to the seventh database, the first element having a homology level above a predetermined homology level with the second element, to obtain candidate nucleotide targets of one or more candidates HEs.

The method of the invention may further comprise identifying in a tenth or a twelfth database of nucleotide sequences, candidate nucleotide targets of one or more candidate HEs, the method comprising:
(A):
(a) for each candidate HEG according to the invention, determining a functional set of relatives of the candidate HEG, a nucleotide sequence being an element of the functional set of relatives of a candidate HEG if:
  i) the nucleotide sequence has a first subsequence, the translation of the first subsequence having a homology level with at least a subsequence of the candidate HE encoded by the candidate HEG above a predetermined homology level, and
  ii) the nucleotide sequence has one or both of the following:
    a second subsequence upstream to the first subsequence, the translation of the second subsequence having a homology level above a predetermined homology level with the translation of a nucleotide sequence containing a 5' half target, the nucleotide sequence containing the 5' half target belonging to the hosting sequence, and
    a third subsequence downstream to the first subsequence, the translation of the third subsequence having a homology level above a predetermined homology level with the translation of a nucleotide sequence containing a 3' half target, the nucleotide sequence containing the 3' half target belonging to the hosting sequence,
(b) for each element in the set of functional relatives of a candidate HEG, predicting an amino acid target of a HE encoded by a functional relative, or an amino acid half target of a HE encoded by a functional relative, in a process comprising:
  i) if the third subsequence is absent, defining a functional N' amino acid half target to be the translation of the second subsequence,
  ii) if the second subsequence is absent, defining a functional C' amino acid half target to be the translation of the third subsequence,
  iii) if both the second and third subsequences are present, defining a functional amino acid target to be the union of the translation of the second subsequence and the translation of the third subsequence,
(c) for each candidate HEG, performing multiple alignment and phylogenetic reconstruction of a set of amino acid sequences comprised of
  i) the candidate HE encoded by the candidate HEG, and
  ii) the translations of the reading frames including the first subsequences of the nucleotide sequences belonging to the functional set of relatives of the candidate HEG,
(d) for each candidate HEG, superimposing the functional amino acid targets and functional amino acid half targets of the HEs encoded by the functional relatives of the candidate HEG on the phylogenetic tree and performing ancestry sequence reconstruction of the predicted amino acid targets of the HEs encoded by the ancestors of the candidate HEG;
(e) generating a ninth database of elements, each element being a pair of the ninth database and comprised of a candidate HEG and the target matrix of the candidate HE encoded by the candidate HEG, the target matrix having an integer N of rows designated 1 to N corresponding to N amino acids and A columns designated: 1 to A, corresponding to the N' to C' positions along the amino acid target of the candidate HE, each element $a_{xy}$ located in the xth row and the yth column of the matrix, where x is an integer from 1 to N and y is an integer from 1 to A, being a number positively correlated with any one or more of the following:
  i) the presence of amino acid x at position y along the amino acid target of the candidate HE, and
  ii) the extent of evolutionary relatedness between the candidate HE and the nearest ancestor of the candidate HE having amino acid x at position y along the predicted amino acid target of the nearest ancestor HE, and iii) the level of confidence in the prediction that a specific ancestor of a candidate HE has amino acid x at position y along the functional amino acid target of the ancestor HE, and iv) the extent of chemical similarity between the amino acid x and the amino acid found at position y of the amino acid target of the candidate HE.

(f) assigning a score to each of one or more pairs consisting of:
  i. a first element being a pair belonging to the ninth database, and
  ii. a second element being a numbered amino acid sequence, the sequence belonging to the six frame translation of a tenth database of nucleotide sequences, the positions of the numbered amino acid sequence being numbered from k to 1 from the N' end to the C' end wherein: $k \geq 1$, and $1 \leq A$;

(g) for each of one or more of the scored pairs having a score above a predetermined threshold, retrieving one or more nucleotide sequences encoding the second element of the scored pair, to obtain the candidate nucleotide targets of one or more candidate HEs, or (B)

(a) for each candidate HEG obtained according to the invention, determining a functional set of relatives of the candidate HEG, a nucleotide sequence being an element of the functional set of relatives of a candidate HEG; if
  i) the nucleotide sequence has a first subsequence, the translation of the first subsequence having a homology level with at least a subsequence of the candidate HE encoded by the candidate HEG above a predetermined homology level, and
  ii) the nucleotide sequence has one or both of the following:
    a second subsequence upstream to the first subsequence, the second subsequence having a homology level above a predetermined homology level with a nucleotide sequence containing a 5' half target, the sequence containing the 5' half target belonging to the hosting sequence, and
    a third subsequence downstream to the first subsequence, the third subsequence having a homology level above a predetermined homology level with a nucleotide sequence containing a 3' half target, the nucleotide sequence containing the 3' half target belonging to the hosting sequence, (b) for each element in the set of functional relatives of a candidate HEG, predicting a functional nucleotide sequence containing a nucleotide target of a HE encoded by a functional relative, or a functional nucleotide sequence containing a nucleotide half target of a HE encoded by a functional relative as follows:
  i) if the third subsequence is absent, defining a functional nucleotide sequence containing a nucleotide 5' half target to be the second subsequence,
  ii) if the second subsequence is absent, defining a functional nucleotide sequence containing the nucleotide 3' half target to be the third subsequence,
  iii) if both the second and third subsequences are present, defining a functional nucleotide sequence containing the nucleotide target to be the union of the second subsequence and the third subsequence, (c) for each candidate HEG, performing multiple alignment and phylogenetic reconstruction of a set of amino acid sequences comprised of
  i) the candidate HE encoded by the candidate HEG, and
  ii) the translations of the reading frames including the first subsequences of the nucleotide sequences belonging to the functional set of relatives of the candidate HEG, (d) for each candidate HEG, superimposing the functional nucleotide sequences containing the nucleotide targets and nucleotide half targets of the HEs encoded by the functional relatives of the candidate HEG on the phylogenetic tree and performing ancestry sequence reconstruction of the predicted nucleotide sequences containing the nucleotide targets of the HEs encoded by the ancestors of the candidate HEG;

(e) generating an eleventh database of elements, each element being a pair of the eleventh database being comprised of a candidate HEG and the target matrix of the candidate HE encoded by the candidate HEG, the target matrix having 4 rows corresponding to the deoxynucleotides adenosine cytosine, guanosine and thymidine and A columns designated: 1 . . . A, corresponding to the 5' to 3' positions along the nucleotide sequence containing the nucleotide target of the candidate HE, each element $a_{xy}$ located in the xth row and the yth column of the matrix being a number positively correlated with any one or more of the following:
  i) the presence of deoxynucleotide x at position y along the nucleotide sequence containing the nucleotide target of the candidate HE, and
  ii) the extent of evolutionary relatedness between the candidate HE and the nearest ancestor of the candidate HE having deoxynucleotide x at position y along the predicted nucleotide sequence containing the nucleotide target of the nearest ancestor HE, and
  iii) the level of confidence in the prediction that a specific ancestor of a candidate HE has deoxynucleotide x at position y along the predicted nucleotide sequence containing the nucleotide target of the ancestor HE, (f) assigning a score to for each of one or more pairs consisting of:
  i. a first element being a pair belonging to the eleventh database, and
  ii. a second element being a numbered nucleotide sequence, the nucleotide sequence belonging to a twelfth database of nucleotide sequences, the positions of the sequence being numbered from k to 1 from the 5' end to the 3' end wherein: $k \geq 1$, and $1 \leq A$ (g) the set of candidate nucleotide targets of one or more candidate HEs being comprised of the second elements of the pairs scored in step (B)(f) having a score above a predetermined threshold.

In another of its aspects, the invention provides a method for identifying in a thirteenth database of nucleotide sequences, candidate nucleotide targets of one or more predetermined HEs, comprising:

(a) generating a fourteenth database of elements, each element of the fourteenth database being a pair comprised of a predetermined HE and the amino acid target of the HE of the element of the fourteenth database, the predetermined HE being encoded by a predetermined HEG residing in a protein coding gene, and the amino acid target being an amino acid sequence encoded by a predetermined nucleotide sequence containing a cognate target of the predetermined HE, wherein, the translation of the predetermined nucleotide sequence containing the cognate target is in a predetermined reading frame.

(b) performing a search for matches between the thirteenth database and the six frame translation of the thirteenth database, a match being a pair comprised of a first element being the amino acid target of a pair in the fourteenth database and a second element belonging to the six frame translation of the twelfth database, the first element having a homology level above a predetermined homology level with the second element; and for each match generated by the search retrieving the nucleotide sequence encoding the second element of the match, to obtain candidate nucleotide targets of the one or more predetermined HEs.

The method may further comprise identifying in a sixteenth or an eighteenth database of nucleotide sequences, candidate nucleotide targets of one or more predetermined HEs, the method comprising:

(A):
(a) for each predetermined HEG residing in a protein encoding gene, determining a functional set of relatives of the predetermined HEG, a nucleotide sequence being an element of the functional set of relatives of a predetermined HEG if:
  i) the nucleotide sequence has a first subsequence, the translation of the first subsequence having a homology level with at least a subsequence of the predetermined HE encoded by the predetermined HEG above a predetermined homology level, and
  ii) the nucleotide sequence has one or both of the following:
    a second subsequence upstream to the first subsequence, the translation of the second subsequence having a homology level above a predetermined homology level with the translation of a predetermined nucleotide sequence containing a 5' half target, and
    a third subsequence downstream to the first subsequence, the translation of the third subsequence having a homology level above a predetermined homology level with the translation of a predetermined nucleotide sequence containing a 3' half target,
(b) for each element in the set of functional relatives of a predetermined HEG, predicting an amino acid target of a HE encoded by a functional relative, or an amino acid half target of a HE encoded by a functional relative, in a process comprising:
  i) if the third subsequence is absent, defining a functional N' amino acid half target to be the translation of the second subsequence,
  ii) if the second subsequence is absent, defining a functional C' amino acid half target to be the translation of the third subsequence,
  iii) if both the second and third subsequences are present, defining a functional amino acid target to be the union of the translation of the second subsequence and the translation of the third subsequence,
(c) for each predetermined HEG, performing multiple alignment and phylogenetic reconstruction of a set of amino acid sequences comprised of
  i) the predetermined HE encoded by the predetermined HEG, and
  ii) the translations of the reading frames including the first subsequences of the nucleotide sequences belonging to the functional set of relatives of the predetermined HEG,
(d) for each predetermined HEG, superimposing the functional amino acid targets and functional amino acid half targets of the HEs encoded by the functional relatives of the predetermined HEG on the phylogenetic tree and performing ancestry sequence reconstruction of the predicted amino acid targets of the HEs encoded by the ancestors of the predetermined HEG;
(e) generating the fifteenth database of elements, each element being a pair of the fifteenth database and comprised of a predetermined HEG and the target matrix of the predetermined HE encoded by the predetermined HEG, the target matrix having an integer N of rows designated 1 to N corresponding to N amino acids and A columns designated: 1 to A, corresponding to the N' to C' positions along the amino acid target of the predetermined HE, each element $a_{x,y}$ located in the xth row and the yth column of the matrix, where x is an integer from 1 to N and y is an integer from 1 to A, being a number positively correlated with any one or more of the following:
  i) the presence of amino acid x at position y along the amino acid target of the predetermined HE, and
  ii) the extent of evolutionary relatedness between the predetermined HE and the nearest ancestor of the predetermined HE having amino acid x at position y along the predicted amino acid target of the nearest ancestor HE, and
  iii) the level of confidence in the prediction that a specific ancestor of a predetermined HE has amino acid x at position y along the functional amino acid target of the ancestor HE, and
  iv) the extent of chemical similarity between the amino acid x and the amino acid found at position y, of the amino acid target of the predetermined HE.
(f) assigning a score to each of one or more pairs consisting of:
  i. a first element being a pair belonging to the fifteenth database, and
  ii. a second element being a numbered amino acid sequence, the sequence belonging to the six frame translation of a sixteenth database of nucleotide sequences, the positions of the numbered amino acid sequence being numbered from k to 1 from the N' end to the C' end wherein: k≥1, and 1≤A;
(g) for each of one or more of the scored pairs having a score above a predetermined threshold, retrieving one or more nucleotide sequences encoding the second element of the scored pair, to obtain the candidate nucleotide targets of one or more predetermined HEs, or (B)
(a) for each predetermined HEG obtained, determining a functional set of relatives of the predetermined HEG, a nucleotide sequence being an element of the functional set of relatives of a predetermined HEG; if
  i) the nucleotide sequence has a first subsequence, the translation of the first subsequence having a homology level with at least a subsequence of the predetermined HE encoded by the predetermined HEG above a predetermined homology level, and
  ii) the nucleotide sequence has one or both of the following:
  a second subsequence upstream to the first subsequence, the second subsequence having a homology level above a predetermined homology level with a nucleotide sequence containing a 5' half target, the sequence containing the 5' half target belonging to the hosting sequence, and
  a third subsequence downstream to the first subsequence, the third subsequence having a homology level above a predetermined homology level with a nucleotide sequence containing a 3' half target, the nucleotide sequence containing the 3' half target belonging to the hosting sequence, (b) for each element in the set of functional relatives of a predetermined HEG, predicting a functional nucleotide sequence containing a nucleotide target of a HE encoded by a functional relative, or a functional nucleotide sequence containing a nucleotide half target of a HE encoded by a functional relative as follows:

i) if the third subsequence is absent, defining a functional nucleotide sequence containing a nucleotide 5' half target to be the second subsequence, ii) if the second subsequence is absent, defining a functional nucleotide sequence containing the nucleotide 3' half target to be the third subsequence, iii) if both the second and third subsequences are present, defining a functional nucleotide sequence containing the nucleotide target to be the union of the second subsequence and the third subsequence, (c) for each predetermined HEG, performing multiple alignment and phylogenetic reconstruction of a set of amino acid sequences comprised of i) the predetermined HE encoded by the predetermined HEG, and ii) the translations of the reading frames including the first subsequences of the nucleotide sequences belonging to the functional set of relatives of the predetermined HEG, (d) for each predetermined HEG, superimposing the functional nucleotide sequences containing the nucleotide targets and nucleotide half targets of the HEs encoded by the functional relatives of the predetermined HEG on the phylogenetic tree and performing ancestry sequence reconstruction of the predicted nucleotide sequences containing the nucleotide targets of the HEs encoded by the ancestors of the predetermined HEG;

(e) generating a seventeenth database of elements, each element being a pair of the seventeenth database being comprised of a predetermined HEG and the target matrix of the predetermined HE encoded by the predetermined HEG, the target matrix having 4 rows corresponding to deoxynucleotides adenosine cytosine, guanosine and thymidine and A columns designated: 1 . . . A, corresponding to the 5' to 3' positions along the nucleotide sequence containing the nucleotide target of the predetermined HE, each element $a_{xy}$ located in the xth row and the yth column of the matrix being a number positively correlated with any one or more of the following:

i) the presence of deoxynucleotide x at position y along the nucleotide sequence containing the nucleotide target of the predetermined HE, and ii) the extent of evolutionary relatedness between the predetermined HE and the nearest ancestor of the predetermined HE having deoxynucleotide x at position y along the predicted nucleotide sequence containing the nucleotide target of the nearest ancestor HE, and iii) the level of confidence in the prediction that a specific ancestor of a predetermined HE has deoxynucleotide x at position y along the predicted nucleotide sequence containing the nucleotide target of the ancestor HE, (f) assigning a score to for each of one or more pairs consisting of:

i. a first element being a pair belonging to the seventeenth database, and ii. a second element being a numbered nucleotide sequence, the nucleotide sequence belonging to a eighteenth database of nucleotide sequences, the positions of the sequence being numbered from k to 1 from the 5' end to the 3' end wherein: k≥1, and 1≤A (g) the set of candidate nucleotide targets of one or more predetermined HEs being comprised of the second elements of the pairs scored in step (B)(f) having a score above a predetermined threshold; and (h) displaying the results on a display device;

(i) The method of the invention may further comprise:

(a) amplification of nucleotide sequences from one or more environmental samples using a pair of a first primer and a second primer, the first primer designed according to a nucleotide sequence containing a nucleotide 5' half target of a candidate HE obtained by the method of the invention or designed according to a predetermined nucleotide sequence containing a nucleotide 5' half target of a predetermined HE obtained by the method of the invention and the second primer designed according to a nucleotide sequence containing a nucleotide 3' half target of a candidate HE obtained by the method of the invention or designed according to a predetermined nucleotide sequence containing a nucleotide 3' half target of a predetermined HE obtained by the method of the invention, wherein the environmental samples is chosen based upon one or more habitats from which the candidate HEG or predetermined HEG encoding the candidate HE or predetermined HE was purified, amplified and sequenced; and (b) cloning the amplified sequences on one or more predetermined vectors The method of the invention may further comprise engineering a final HE capable of cleaving a nucleotide sequence selected from the sixth database, the seventh database, the tenth database, or the twelfth database, or a candidate nucleotide target of one or more predetermined HEs, the candidate nucleotide target being identified in the thirteenth database by the method of the invention or a candidate nucleotide target of one or more predetermined HEs the candidate nucleotide target being identified in the sixteenth database or in the eighteenth database by the method of the invention, wherein the engineering comprises subjecting a candidate HE or predetermined HE to a process of directed evolution and rational design to generate the final HE capable of cleaving the nucleotide sequence or the candidate nucleotide target of the predetermined HE.

In the method of the invention, any one of the first database, the second database or the third database may be a database stored on a storage medium selected from:

(a) nt, (b) env nt, and (c) a union of nt and env nt.

In the method of the invention, any one of the sixth database, the seventh database, tenth database, the twelfth database, the thirteenth database, the sixteenth database, and the eighteenth database may be selected from:

a) a subset of the human genome database;

b) a set of sequences comprising genes found in the OMIM database;

c) a set of sequences comprising genes found in the OMIM database including introns, and flanking regions;

d) a database stored on a storage medium comprising one or more gene sets of one or more model organisms, e) a database stored on a storage medium comprising one or more gene sets of one or more plants;

f) a database stored on a storage medium comprising one or more gene sets of one or more domesticated animals; and g) a database stored on a storage medium comprising one or more gene sets of one or more microorganisms used in the biotechnological industry;

h) a database stored on a storage medium of genes of human pathogens.

In the method of the invention, assigning a score to each of one or more fourth pairs may comprise:

(a) for every x belonging to {k . . . 1} assigning a score to position x of the second element of the fourth pair, the score being positively correlated with the element $a_{xy}$ of the matrix being the second element of the third pair, wherein y is the amino acid present at position x of the second element of the fourth pair (b) assigning a score to the fourth pair, the score of the fourth pair being positively correlated with any one or more of the following:

i) the score of each position along the second element of the fourth pair.
  ii) the size of 1-k+1
  iii) the score of each position along a functional second element, the first element and the functional second element constituting a functional fourth pair, the functional second element being a 1-k+1 long predetermined amino acid target of a predetermined HE, the predetermined amino acid target being numbered from k to 1 from the N' end to the C' end.
  iv) an extent of similarity between patterns found in the second element of the fourth pair and patterns found in amino acids targets of a predetermined family of HEs containing a common amino acid motif found in the candidate HE being the first element of the third pair;
  v) an extent of similarity at the nucleotide level at each position along the second element of the fourth pair between the codons encoding the amino acid in the second element of the fourth pair at the position and codons encoding one or more alternative amino acids that would attribute a higher score when present at the position.

Assigning a score to each of one or more sixth pairs may comprise:

(a) For every x belonging to {k . . . 1} assigning a score to position x of the second element of the sixth pair, the score being positively correlated with the element $a_{xy}$ of the matrix being the second element of the fifth pair, wherein y is the deoxynucleotide present at position x of the second element of the sixth pair (b) Assigning a score to the sixth pair, the score of the sixth pair being positively correlated with any one or more of the following:

i) the score of each position along the second element of the sixth pair.
  ii) the size of 1-k+1
  iii) the score of each position along a functional second element, the first element and the functional second element constituting a functional sixth pair, the functional second element being a 1-k+1 long predetermined nucleotide target of a predetermined HE, the predetermined nucleotide target being numbered from k to 1 from the 5' end to the 3' end.
  iv) an extent of similarity between patterns found in the second element of the sixth pair and patterns found in nucleotide targets of a predetermined family of HEs containing a common amino acid motif found in the candidate HE being the first element of the fifth pair.

Assigning a score to each of one or more tenth pairs may comprise:

(a) For every x belonging to {k . . . 1} assigning a score to position x of the second element of the tenth pair, the score being positively correlated with the element $a_{xy}$ of the matrix being the second element of the ninth pair, wherein y is the amino acid present at position x of the second element of the tenth pair (b) Assigning a score to the tenth pair, the score of the tenth pair being positively correlated with any one or more of the following:

i) the score of each position along the second element of the tenth pair.
  ii) the size of 1-k+1
  iii) the score of each position along a functional second element, the first element and the functional second element constituting a functional tenth pair, the functional second element being a 1-k+1 long predetermined amino acid target of a predetermined HE, the predetermined amino acid target being numbered from k to 1 from the N' end to the C' end;
  iv) an extent of similarity between patterns found in the second element of the tenth pair and patterns found in amino acids targets of a predetermined family of HEs containing a common amino acid motif found in the predetermined HE being the first element of the ninth pair;
  v) an extent of similarity at the nucleotide level at each position along the second element of the tenth pair between the codons encoding the amino acid in the second element of the tenth pair at the position and codons encoding one or more alternative amino acids that would attribute a higher score when present at the position.

Assigning a score to each of one or more twelfth pairs may comprise:

(a) for every x belonging to {k . . . 1} assigning a score to position x of the second element of the twelfth pair, the score being positively correlated with the element $a_{xy}$ of the matrix being the second element of the eleventh pair, wherein y is the deoxynucleotide present at position x of the second element of the twelfth pair (b) assigning a score to the twelfth pair, the score of the twelfth pair being positively correlated with any one or more of the following:

i) the score of each position along the second element of the twelfth pair.
  ii) the size of 1-k+1
  iii) the score of each position along a functional second element, the first element and the functional second element constituting a functional twelfth pair, the functional second element being a 1-k+1 long predetermined nucleotide target of a predetermined HE, the predetermined nucleotide target being numbered from k to 1 from the 5' end to the 3' end.
  iv) an extent of similarity between patterns found in the second element of the twelfth pair and patterns found in nucleotide targets of a predetermined family of HEs containing a common amino acid motif found in the predetermined HE being the first element of the eleventh pair.

A score may be assigned to each of one or more eighth pairs of a first element from the eleventh database and a second element from the twelfth database, wherein the amino acid target of the first element has a homology level with the second element above the predetermined homology level. The score may be positively correlated with any one or more of the following:
  (a) a level of homology between the amino acid target of the first element and the second element;
  (b) a similarity between a segment within the amino acid target of the first element and a target of a predetermined HEG having a homology level above a predetermined level with the HEG of the first element, wherein the segment and the second element have a homology level above a predetermined homology level,
  (c) an extent of similarity between patterns found in a segment of the amino acid target of the first element and patterns found in amino acids targets of a predetermined family of HEs containing a common amino acid motif found in the predetermined HE encoded by the predetermined HEG of the first element, wherein the segment and the second element have a homology level above a predetermined homology level;
  (d) an extent of similarity at the nucleotide level between codons of mismatched amino acids in the alignment of a segment of the amino acid target of the first element and the second element.

The invention also provides a processor configured to carry out the method of the invention.

The invention further provides pharmaceutical composition comprising a HEG obtained by the method of the invention together with a pharmaceutically acceptable carrier. The invention also provides an agricultural composition comprising a HEG obtained by the method of the invention.

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 4 shows the cleaving activity of the HEs PI-SceI (FIG. 4a) on wild-type target (SEQ ID NO: 3), 13-transition target (SEQ ID NO: 4), and missense target (SEQ ID NO: 5) and PI-PspI (FIG. 4b) on wild-type target (SEQ ID NO: 8), 13-transition target (SEQ ID NO: 9), and missense target (SEQ ID NO: 10).

DETAILED DESCRIPTION OF EMBODIMENTS

Figure 1:
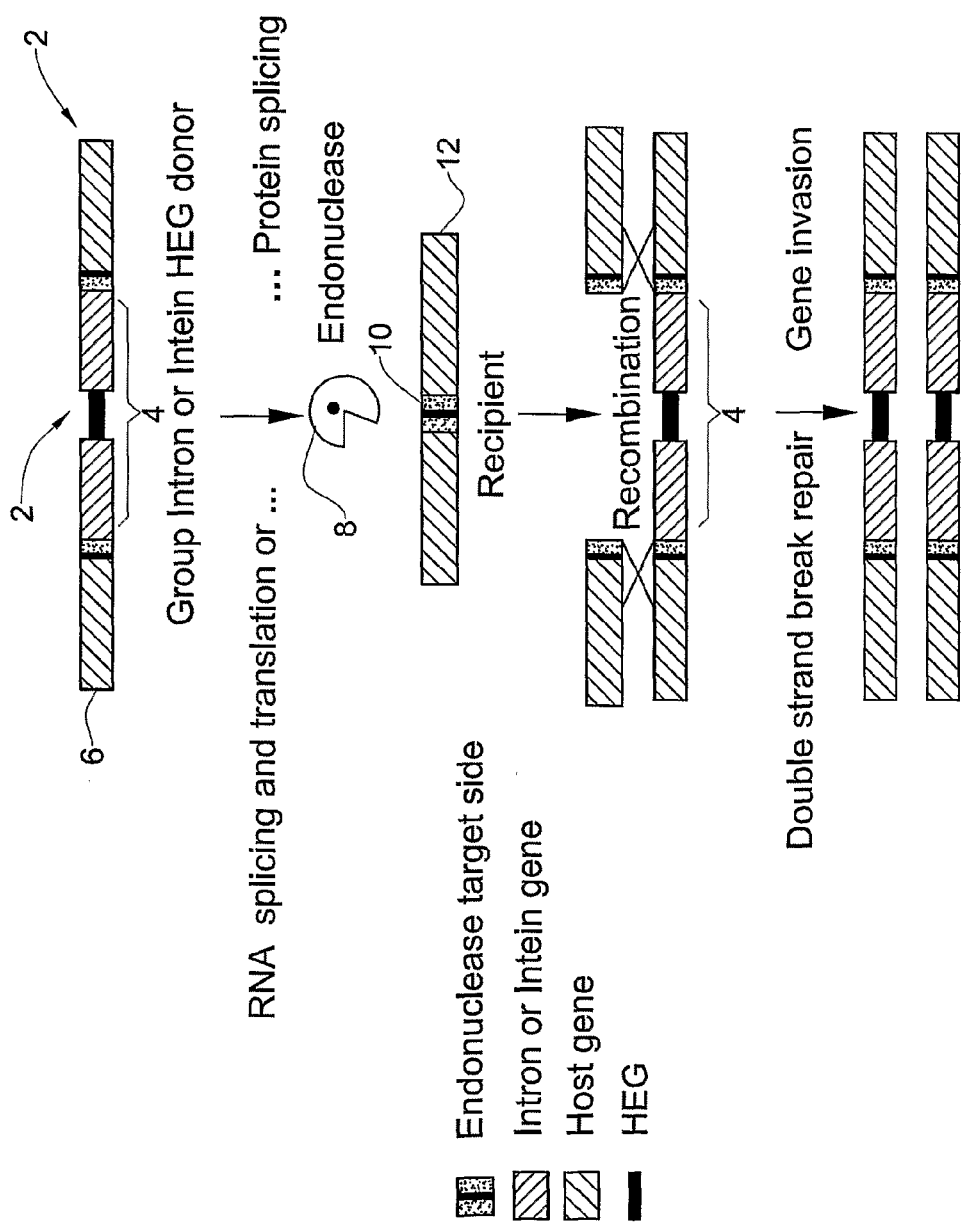
FIG. 1 is a schematic diagram of expression of a HEG.
Figure 2:
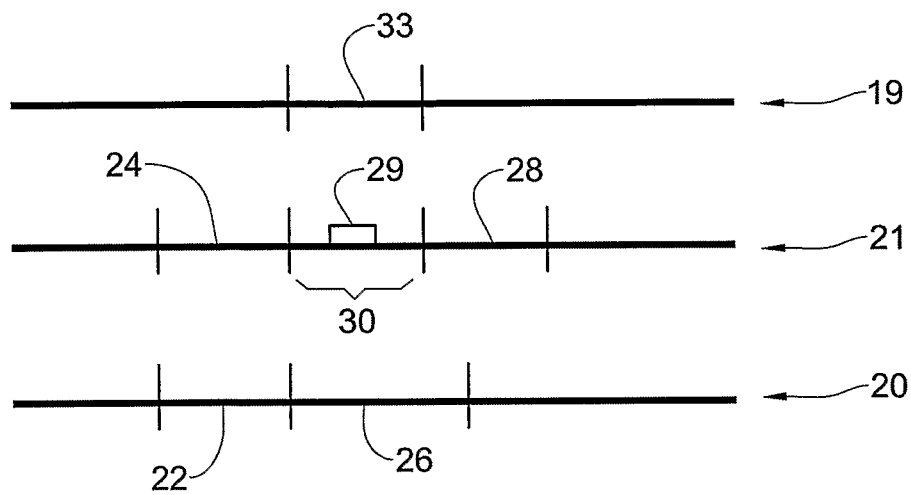
FIG. 2 shows the structure of a protein coding vacant homolog.
Figure 3:
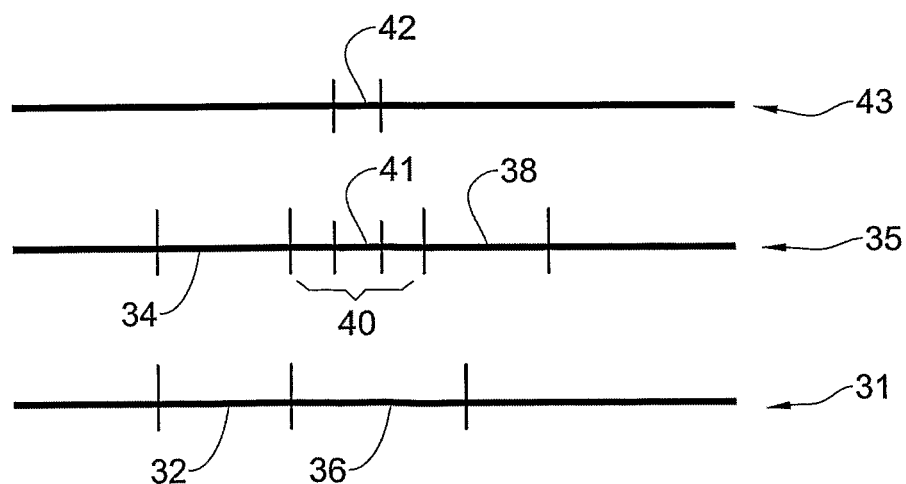
FIG. 3 shows an RNA coding vacant homologue.

The target specificity of two commercially available HEs, PI-SceI and PI-PspI (FIGS. 4a and 4b respectively) were examined by determining the cleavage efficiency of these HEs on their cognate targets as well as on synthetic targets where all wobble positions underwent synonymous substitutions. PI-SceI is encoded by SEQ ID NO: 1, having the amino acid sequence SEQ ID NO: 2. PI-PspI is encoded by SEQ ID NO: 6, having the amino acid sequence SEQ ID NO: 7. The targets were cloned on a pGEM-Teasy vector which was later fragmented by a restriction enzyme in order to make cleavage by the HE more visually pronounced. As shown in FIG. 4, PI-SceI cleaves a target bearing 13 synonymous substitutions as efficiently it is does its cognate target, while a single non-synonymous mutation can eliminate cleavage entirely (FIG. 4a). Similarly, PI-PspI efficiently cleaves a synthetic target that differs from its cognate target by 10 synonymous substitutions. In this case, a single non-synonymous mutation reduced cleavage by more than 80% (FIG. 4b). It is important to note that PI-SceI and PI-PspI inhabit species from two different domains of life, Eukaria and Archaea respectively.

The invention claimed is:

1. A computer implemented method, implemented by a processor, for generating a first set of hosting sequences, the hosting sequences being nucleotide sequences containing candidate homing endonuclease genes (HEGs) or a second set of hosting sequences, comprising:
   (a) an act of the processor performing a first search on a plurality of amino acid sequences generated from all possible six frame translations of one or more nucleotide sequences of a first database stored on a storage medium for amino acid sequences having at least one subsequence having at least a predetermined homology level with the translation of at least one subsequence of one or more predetermined HEGs; and, for each amino acid sequence generated by the search, retrieving from the first database one or more nucleotide sequences encoding the amino acid sequence, to generate a first set of search results;
   (b) an act of the processor performing a search selected from:
      (i) a second search on the amino acid sequences generated from all of the six frame translations of the nucleotide sequences of a second database stored on a storage medium for amino acid sequences having at least one subsequence having at least a predetermined homology level with at least one subsequence of at least one of the six frame translations of at least one sequence belonging to the first set of search results; and, for every amino acid sequence generated by the second search, retrieving from the second database one or more nucleotide sequences encoding the amino acid sequence, to generate a second set of search results, and
      (ii) a third search in a third database of nucleotide sequences stored on a storage medium for nucleotide sequences having at least one subsequence having at least a predetermined homology level with at least one subsequence of a sequence belonging to the first set of search results, to generate a third set of search results; and
   (c) an act of the processor generating the first set of hosting sequences in a process involving identifying in the second set of search results one or more protein coding vacant homologs for each of one or more sequences of the first set of search results, or
   generating the second set of hosting sequences in a process involving identifying in the third set of search results one or more RNA coding vacant homologs for each of one or more sequences of the first set of search results;
   wherein
   a protein coding vacant homolog being a nucleotide sequence belonging to the second set of search results for which at least one of the six frame translations of the sequence from the second set of search results includes a first interval having at least a predetermined homology level with a second interval of one of the six frame translations of the sequence belonging to the first set of search results, and the translation of the sequence from the second set of search results further having a third interval C' and adjacent to the first interval, the third interval having at least a predetermined homology level with a fourth interval in one of the six frame translations of the sequence belonging to the first set of search results, the nucleotide sequences encoding the second and fourth intervals being separated by a fifth interval, the fifth interval containing a subinterval, the translation of the subinterval having at least a predetermined homology level with a sixth interval of the translation of one or more predetermined HEGs, and the fifth interval is longer than a predetermined threshold,
   and wherein
   an RNA coding vacant homolog being a sequence belonging to the third set of search results including a first interval having at least a predetermined homology level with a second interval of the sequence belonging to the first set of search results, and the sequence from the third set of search results further having a third interval downstream and adjacent to the first interval having at least a predetermined homology level with a fourth interval in the sequence belonging to the first set of search results, the second and forth intervals being separated by a fifth interval, the fifth interval containing a subinterval, the translation of the subinterval having at least a predetermined homology level with a sixth interval of the translation of one or more predetermined HEGs, and the fifth interval is longer than a predetermined threshold.

2. The method according to claim 1, further comprising, an act of the processor filtering from the first set of hosting sequences containing candidate HEGs those sequences not satisfying at least one of the following conditions:
   i) the translations of both the first and the second intervals according to the homologous reading frames are continuous and longer than a predetermined threshold; and
   ii) the translations of both the third and the fourth intervals according to the homologous reading frames are continuous and longer than a predetermined threshold.

3. The method according to claim 1 further generating from the first set of hosting sequences, a first set of candidate HEGs comprising candidate HEGs residing in inteins.

4. The method according to claim 1 further generating from the first set of hosting sequences, a second set of candidate HEGs comprising candidate HEGs residing in introns of protein coding genes.

5. The method according to claim 3 wherein the first set of candidate HEGs comprises the fifth interval of one or more of the nucleotide sequences belonging to the first set of hosting sequences for each nucleotide sequence in the first set of hosting sequences for which the fifth interval is in the same open reading frame as the nucleotide sequences encoding the second and fourth intervals of the nucleotide sequence in the first set of hosting sequences.

6. The method according to claim 4 wherein the second set comprises one or more nucleotide sequences each of which is a subsequence of a fifth interval of a nucleotide sequence belonging to the first set of hosting sequences, wherein the fifth interval is not in the reading frame of either one or both of the nucleotide sequences encoding the second and fourth intervals of the nucleotide sequence in the first set of hosting sequences, and the subsequence is an open reading frame beginning with a start codon and ending with a stop codon, and the subsequence being longer than a predetermined threshold.

7. The method according to claim 1 further comprising identifying a third set of candidate HEGs residing in introns of RNA genes, the third set of candidate HEGs comprising one or more nucleotide sequences, each sequence being a subsequence of a fifth interval of a nucleotide sequence belonging to the second set of hosting sequences, wherein the fifth interval is not in the reading frame of either one or both of the nucleotide sequences encoding the second and fourth intervals of the nucleotide sequence belonging to the second set of hosting sequences, and the subsequence is an open reading frame beginning with a start codon and ending with a stop codon, and the subsequence being longer than a predetermined threshold.

8. The method according to claim 1 further comprising an act of the processor filtering the first set of hosting sequences or the second set of hosting sequences, comprising:
   (a) for each of one or more nucleotide sequences belonging to the first set of hosting sequences, an act of the processor calculating a Ka\Ks ratio based upon multiple alignment and phylogenetic reconstruction of a set of amino acid sequences, wherein the calculating comprises:
      i) the homing endonuclease (HE) encoded by the candidate HEG of the hosting sequence, and
      ii) a set of intervals found within the translation of nucleotide sequences in the second set of search results, each interval having a homology level above a predetermined homology level with the translation of at least a subsequence of the fifth interval of the nucleotide sequence belonging to the first set of hosting sequences; and
      iii) filtering out from the first set of hosting sequences nucleotide sequences containing degenerate candidate HEGs, a nucleotide sequence containing a degenerate candidate HEG having Ka/Ks ratio above a predetermined level; or
   (b) for each of one or more sequences belonging to the second set of hosting sequences, an act of the processor calculating a Ka\Ks ratio based upon multiple alignment and phylogenetic reconstruction of a set of amino acid sequences comprising:
      i) the candidate HE encoded by the candidate HEG of the hosting sequence, and
      ii) a set of intervals found within the translation of nucleotide sequences in the second set of search results or in the third set of search results, each interval having a homology level above a predetermined threshold with the translation of at least a subsequence of the fifth interval of the nucleotide sequence belonging to the second set of hosting sequences; and
      iii) filtering out from the second set of hosting sequences, nucleotide sequences containing degenerate candidate HEGs, a nucleotide sequence containing a degenerate candidate HEG having Ka/Ks ratio above a predetermined level.

9. The method according to claim 1 comprising an act of the processor determining a nucleotide sequence containing a cognate target of a candidate homing endonuclease (HE) encoded by a candidate HEG, the nucleotide sequence being a union of a nucleotide sequence containing a 5' half target and a nucleotide sequence containing a 3' half target, the nucleotide sequence containing the 5' half target being a nucleotide sequence of predetermined length upstream and adjacent to the 5' end of the fifth interval of the hosting sequence, and the nucleotide sequence containing the 3' half target being a nucleotide sequence of predetermined length downstream and adjacent to a 3' end of the fifth interval of the hosting sequence.

10. The method according to claim 9, further comprising
   (a) an act of the processor generating a fourth database stored on a storage medium of elements, each element being a pair of the fourth database and comprised of a candidate HE and the amino acid target of the HE of the pair of the fourth database, the candidate HE being encoded by a candidate HEG, and the amino acid target being an amino acid sequence encoded by a nucleotide sequence containing a cognate target of the candidate HE obtained by the method according to claim 9, wherein, the translation of the sequence containing the cognate target is in the reading frame defining the homology between the translation of the first interval and the translation of the second interval; or
   (b) an act of the processor generating a fifth database stored on a storage medium of elements, each element being a pair of the fifth data base and comprised of a candidate HE and the target of the HE of the pair of the fifth database the candidate HE being encoded by a candidate HEG, and the target of the HE being a sequence containing the cognate target obtained by the method according to claim 9.

11. The method according to claim 10 further comprising an act of the processor identifying in a sixth database stored on a storage medium and of nucleotide sequences or a seventh database stored on a storage medium of nucleotide sequences, candidate nucleotide targets of one or more candidates HEs, the method comprising:
   (a) an act of the processor performing a search for matches between the fourth database and the six frame translations of a sixth database stored on a storage medium and, a match being a pair comprised of a first element being the amino acid target of a pair in the fourth database and a second element belonging to the six frame translations of the sixth database, the first element having a homology level above a predetermined homology level with the second element; and for each match generated by the search retrieving the nucleotide sequence encoding the second element of the match, to obtain candidate nucleotide targets of one or more candidates HEs; or
   (b) an act of the processor performing a search for matches between the fifth database and a seventh database stored on a storage medium and, a match being a pair of the seventh database and comprised of a first element being the target of a pair in the fifth database and a second element belonging to the seventh database, the first element having a homology level above a predetermined homology level with the second element, to obtain candidate nucleotide targets of one or more candidates HEs.

12. The method according to claim 10 further comprising an act of the processor identifying in a ninth or a eleventh database of nucleotide sequences, candidate nucleotide targets of one or more candidate HEs, the method comprising:
   (A):
   (a) for each candidate HEG, an act of the processor determining a functional set of relatives of the candidate HEG, a nucleotide sequence being an element of the functional set of relatives of a candidate HEG if:
      i) the nucleotide sequence has a first subsequence, the translation of the first subsequence having a homology level with at least a subsequence of the candidate HE encoded by the candidate HEG above a predetermined homology level, and
      ii) the nucleotide sequence has one or both of the following:
         a second subsequence upstream to the first subsequence, the translation of the second subsequence having a homology level above a predetermined homology level with the translation of a nucleotide sequence containing a 5' half target, the nucleotide sequence containing the 5' half target belonging to the hosting sequence, and
         a third subsequence downstream to the first subsequence, the translation of the third subsequence having a homology level above a predetermined homology level with the translation of a nucleotide sequence containing a 3' half target, the nucleotide sequence containing the 3' half target belonging to the hosting sequence,
   (b) for each element in the set of functional relatives of a candidate HEG, an act of the processor predicting an amino acid target of a HE encoded by a functional relative, or an amino acid half target of a HE encoded by a functional relative, in a process comprising:
      i) if the third subsequence is absent, defining a functional N' amino acid half target to be the translation of the second subsequence,
      ii) if the second subsequence is absent, defining a functional C' amino acid half target to be the translation of the third subsequence,
      iii) if both the second and third subsequences are present, defining a functional amino acid target to be the union of the translation of the second subsequence and the translation of the third subsequence,
   (c) for each candidate HEG, an act of the processor performing multiple alignment and phylogenetic reconstruction of a set of amino acid sequences comprised of
      i) the candidate HE encoded by the candidate HEG, and
      ii) the translations of the reading frames including the first subsequences of the nucleotide sequences belonging to the functional set of relatives of the candidate HEG,
   (d) for each candidate HEG, an act of the processor superimposing the functional amino acid targets and functional amino acid half targets of the HEs encoded by the functional relatives of the candidate HEG on the phylogenetic tree and performing ancestry sequence reconstruction of the predicted amino acid targets of the HEs encoded by the ancestors of the candidate HEG;
   (e) an act of the processor generating a eighth database of elements, each element being a pair of the eighth database and comprised of a candidate HEG and the target matrix of the candidate HE encoded by the candidate HEG, the target matrix having an integer N of rows designated 1 to N corresponding to N amino acids and A columns designated: 1 to A, corresponding to the N' to C' positions along the amino acid target of the candidate HE, each element $a_{xy}$ located in the $x^{th}$ row and the $y^{th}$ column of the matrix, where x is an integer from 1 to N and y is an integer from 1 to A, being a number positively correlated with any one or more of the following:
      i) the presence of amino acid x at position y along the amino acid target of the candidate HE, and
      ii) the extent of evolutionary relatedness between the candidate HE and the nearest ancestor of the candidate HE having amino acid x at position y along the predicted amino acid target of the nearest ancestor HE, and
      iii) the level of confidence in the prediction that a specific ancestor of a candidate HE has amino acid x at position y along the functional amino acid target of the ancestor HE, and
      iv) the extent of chemical similarity between the amino acid x and the amino acid found at position y of the amino acid target of the candidate HE.
   (f) an act of the processor assigning a score to each of one or more pairs consisting of:
      i. a first element being a pair belonging to the eighth database, and
      ii. a second element being a numbered amino acid sequence, the sequence belonging to the six frame translations of a ninth database of nucleotide sequences, the positions of the numbered amino acid sequence being numbered from k to 1 from the N' end to the C' end wherein: k≥1, and 1≤A;
   (g) for each of one or more of the scored pairs having a score above a predetermined threshold, an act of the processor retrieving one or more nucleotide sequences encoding the second element of the scored pair, to obtain the candidate nucleotide targets of one or more candidate HEs, or
   (B)
   (a) for each candidate HEG, an act of the processor determining a functional set of relatives of the candidate HEG, a nucleotide sequence being an element of the functional set of relatives of a candidate HEG; if
  i) the nucleotide sequence has a first subsequence, the translation of the first subsequence having a homology level with at least a subsequence of the candidate HE encoded by the candidate HEG above a predetermined homology level, and
  ii) the nucleotide sequence has one or both of the following:
    a second subsequence upstream to the first subsequence, the second subsequence having a homology level above a predetermined homology level with a nucleotide sequence containing a 5' half target, the sequence containing the 5' half target belonging to the hosting sequence, and
    a third subsequence downstream to the first subsequence, the third subsequence having a homology level above a predetermined homology level with a nucleotide sequence containing a 3' half target, the nucleotide sequence containing the 3' half target belonging to the hosting sequence,
(b) for each element in the set of functional relatives of a candidate HEG, an act of the processor predicting a functional nucleotide sequence containing a nucleotide target of a HE encoded by a functional relative, or a functional nucleotide sequence containing a nucleotide half target of a HE encoded by a functional relative as follows:
  i) if the third subsequence is absent, defining a functional nucleotide sequence containing a nucleotide 5' half target to be the second subsequence,
  ii) if the second subsequence is absent, defining a functional nucleotide sequence containing the nucleotide 3' half target to be the third subsequence,
  iii) if both the second and third subsequences are present, defining a functional nucleotide sequence containing the nucleotide target to be the union of the second subsequence and the third subsequence,
(c) for each candidate HEG, an act of the processor performing multiple alignment and phylogenetic reconstruction of a set of amino acid sequences comprised of
  i) the candidate HE encoded by the candidate HEG, and
  ii) the translations of the reading frames including the first subsequences of the nucleotide sequences belonging to the functional set of relatives of the candidate HEG,
(d) for each candidate HEG, an act of the processor superimposing the functional nucleotide sequences containing the nucleotide targets and nucleotide half targets of the HEs encoded by the functional relatives of the candidate HEG on the phylogenetic tree and performing ancestry sequence reconstruction of the predicted nucleotide sequences containing the nucleotide targets of the HEs encoded by the ancestors of the candidate HEG;
(e) an act of the processor generating an tenth database of elements, each element being a pair of the tenth database being comprised of a candidate HEG and the target matrix of the candidate HE encoded by the candidate HEG, the target matrix having 4 rows corresponding to the deoxynucleotides adenosine cytosine, guanosine and thymidine and A columns designated: 1 . . . A, corresponding to the 5' to 3' positions along the nucleotide sequence containing the nucleotide target of the candidate HE, each element $a_{xy}$ located in the $x^{th}$ row and the $y^{th}$ column of the matrix being a number positively correlated with any one or more of the following:
  i) the presence of deoxynucleotide x at position y along the nucleotide sequence containing the nucleotide target of the candidate HE, and
  ii) the extent of evolutionary relatedness between the candidate HE and the nearest ancestor of the candidate HE having deoxynucloetide x at position y along the predicted nucleotide sequence containing the nucleotide target of the nearest ancestor HE, and
  iii) the level of confidence in the prediction that a specific ancestor of a candidate HE has deoxynucleotide x at position y along the predicted nucleotide sequence containing the nucleotide target of the ancestor HE,
(f) an act of the processor assigning a score to for each of one or more pairs consisting of:
  i. a first element being a pair belonging to the tenth database, and
  ii. a second element being a numbered nucleotide sequence, the nucleotide sequence belonging to a eleventh database of nucleotide sequences, the positions of the sequence being numbered from k to 1 from the 5' end to the 3' end wherein: $k \geq 1$, and $1 \leq A$
(g) the set of candidate nucleotide targets of one or more candidate HEs being comprised of the second elements of the pairs scored in step (B)(f) having a score above a predetermined threshold.

13. A computer implemented method, implemented by a processor, for identifying in a first database of nucleotide sequences, candidate nucleotide targets of one or more predetermined HEs, the method comprising:
(a) an act of the processor of generating a second database of elements, each element of the second database being stored in a storage medium and being a pair comprised of a predetermined HE and the amino acid target of the HE of the element of the second database, the predetermined HE being encoded by a predetermined HEG residing in a protein coding gene, and the amino acid target being an amino acid sequence encoded by a predetermined nucleotide sequence containing a cognate target of the predetermined HE, wherein, the translation of the predetermined nucleotide sequence containing the cognate target is in a predetermined reading frame;
(b) an act of the processor of performing a search for matches between the first database and a plurality of amino acid sequences generated from all possible six frame translations of the nucleotide sequences of the first database, a match being a pair comprised of a first element being the amino acid target of a pair in the second database and a second element belonging to at least one of the six frame translations of the first database, the first element having a homology level above a predetermined homology level with the second element; and for each match generated by the search retrieving the nucleotide sequence encoding the second element of the match, to obtain candidate nucleotide targets of the one or more predetermined HEs; and
(c) an act processor of displaying the results on a display device.

14. The method according to claim 13 further comprising an act of the processor of identifying in a fourth or an sixth database of nucleotide sequences, candidate nucleotide targets of one or more predetermined HEs, the method comprising:
(A):
(a) for each predetermined HEG residing in a protein encoding gene, an act of the processor of determining a functional set of relatives of the predetermined HEG, a nucleotide sequence being an element of the functional set of relatives of a predetermined HEG if:
  i) the nucleotide sequence has a first subsequence, the translation of the first subsequence having a homology level with at least a subsequence of the predetermined HE encoded by the predetermined HEG above a predetermined homology level, and
ii) the nucleotide sequence has one or both of the following:
a second subsequence upstream to the first subsequence, the translation of the second subsequence having a homology level above a predetermined homology level with the translation of a predetermined nucleotide sequence containing a 5' half target, and
a third subsequence downstream to the first subsequence, the translation of the third subsequence having a homology level above a predetermined homology level with the translation of a predetermined nucleotide sequence containing a 3' half target,
(b) for each element in the set of functional relatives of a predetermined HEG, an act of the processor of predicting an amino acid target of a HE encoded by a functional relative, or an amino acid half target of a HE encoded by a functional relative, in a process comprising:
i) if the third subsequence is absent, defining a functional N' amino acid half target to be the translation of the second subsequence,
ii) if the second subsequence is absent, defining a functional C' amino acid half target to be the translation of the third subsequence,
iii) if both the second and third subsequences are present, defining a functional amino acid target to be the union of the translation of the second subsequence and the translation of the third subsequence,
(c) for each predetermined HEG, an act of the processor of performing multiple alignment and phylogenetic reconstruction of a set of amino acid sequences comprised of
i) the predetermined HE encoded by the predetermined HEG, and
ii) the translations of the reading frames including the first subsequences of the nucleotide sequences belonging to the functional set of relatives of the predetermined HEG,
(d) for each predetermined HEG, an act of the processor of superimposing the functional amino acid targets and functional amino acid half targets of the HEs encoded by the functional relatives of the predetermined HEG on the phylogenetic tree and performing ancestry sequence reconstruction of the predicted amino acid targets of the HEs encoded by the ancestors of the predetermined HEG;
(e) an act of the processor of generating the third database of elements, each element being a pair of the third database and comprised of a predetermined HEG and a target matrix of the predetermined HE encoded by the predetermined HEG, the target matrix having an integer N of rows designated 1 to N corresponding to N amino acids and A columns designated: 1 to A, corresponding to the N' to C' positions along the amino acid target of the predetermined HE, each element $a_{xy}$ located in the $x^{th}$ row and the $y^{th}$ column of the matrix, where x is an integer from 1 to N and y is an integer from 1 to A, being a number positively correlated with any one or more of the following:
i) the presence of amino acid x at position y along the amino acid target of the predetermined HE, and
ii) the extent of evolutionary relatedness between the predetermined HE and the nearest ancestor of the predetermined HE having amino acid x at position y along the predicted amino acid target of the nearest ancestor HE, and
iii) the level of confidence in the prediction that a specific ancestor of a predetermined HE has amino acid x at position y along the functional amino acid target of the ancestor HE, and
iv) the extent of chemical similarity between the amino acid x and the amino acid found at position y, of the amino acid target of the predetermined HE.
(f) an act processor of assigning a score to each of one or more pairs consisting of:
i. a first element being a pair belonging to the third database, and
ii, a second element being a numbered amino acid sequence, the sequence belonging to the six frame translation of a fourth database of nucleotide sequences, the positions of the numbered amino acid sequence being numbered from k to 1 from the N' end to the C' end wherein: $k \geq 1$, and $1 \leq A$;
(g) for each of one or more of the scored pairs having a score above a predetermined threshold, an act processor of retrieving one or more nucleotide sequences encoding the second element of the scored pair, to obtain the candidate nucleotide targets of one or more predetermined HEs, or
(B)
(a) for each predetermined HEG obtained, an act of the processor of determining a functional set of relatives of the predetermined HEG, a nucleotide sequence being an element of the functional set of relatives of a predetermined HEG; if
i) the nucleotide sequence has a first subsequence, the translation of the first subsequence having a homology level with at least a subsequence of the predetermined HE encoded by the predetermined HEG above a predetermined homology level, and
ii) the nucleotide sequence has one or both of the following:
a second subsequence upstream to the first subsequence, the second subsequence having a homology level above a predetermined homology level with a nucleotide sequence containing a 5' half target, the sequence containing the 5' half target belonging to the hosting sequence, and
a third subsequence downstream to the first subsequence, the third subsequence having a homology level above a predetermined homology level with a nucleotide sequence containing a 3' half target, the nucleotide sequence containing the 3' half target belonging to the hosting sequence,
(b) for each element in the set of functional relatives of a predetermined HEG, predicting a functional nucleotide sequence containing a nucleotide target of a HE encoded by a functional relative, or a functional nucleotide sequence containing a nucleotide half target of a HE encoded by a functional relative as follows:
i) if the third subsequence is absent, defining a functional nucleotide sequence containing a nucleotide 5' half target to be the second subsequence,
ii) if the second subsequence is absent, defining a functional nucleotide sequence containing the nucleotide 3' half target to be the third subsequence,
iii) if both the second and third subsequences are present, defining a functional nucleotide sequence containing the nucleotide target to be the union of the second subsequence and the third subsequence, (c) for each predetermined HEG, an act of the processor of performing multiple alignment and phylogenetic reconstruction of a set of amino acid sequences comprised of
   i) the predetermined HE encoded by the predetermined HEG, and
   ii) the translations of the reading frames including the first subsequences of the nucleotide sequences belonging to the functional set of relatives of the predetermined HEG,
(d) for each predetermined HEG, an act of the processor of superimposing the functional nucleotide sequences containing the nucleotide targets and nucleotide half targets of the HEs encoded by the functional relatives of the predetermined HEG on the phylogenetic tree and performing ancestry sequence reconstruction of the predicted nucleotide sequences containing the nucleotide targets of the HEs encoded by the ancestors of the predetermined HEG;
(e) an act of the processor of generating a fifth database of elements, each element being a pair of the database being comprised of a predetermined HEG and a target matrix of the predetermined HE encoded by the predetermined HEG, the target matrix having 4 rows corresponding to deoxynucleotides adenosine cytosine, guanosine and thymidine and A columns designated: 1...A, corresponding to the 5' to 3' positions along the nucleotide sequence containing the nucleotide target of the predetermined HE, each element $a_{xy}$ located in the $x^{th}$ row and the $y^{th}$ column of the matrix being a number positively correlated with any one or more of the following:
   i) the presence of deoxynucleotide x at position y along the nucleotide sequence containing the nucleotide target of the predetermined HE, and
   ii) the extent of evolutionary relatedness between the predetermined HE and the nearest ancestor of the predetermined HE having deoxynucloetide x at position y along the predicted nucleotide sequence containing the nucleotide target of the nearest ancestor HE, and
   iii) the level of confidence in the prediction that a specific ancestor of a predetermined HE has deoxynucleotide x at position y along the predicted nucleotide sequence containing the nucleotide target of the ancestor HE,
(f) an act of the processor of assigning a score to for each of one or more pairs consisting of:
   i. a first element being a pair belonging to the fifth database, and
   ii, a second element being a numbered nucleotide sequence, the nucleotide sequence belonging to a sixth database of nucleotide sequences, the positions of the sequence being numbered from k to 1 from the 5' end to the 3' end wherein: k≥1, and 1≤A
(g) the set of candidate nucleotide targets of one or more predetermined HEs being comprised of the second elements of the pairs scored in step (B)(f) having a score above a predetermined threshold.

15. The method according to claim 9 further comprising:
(a) amplification of nucleotide sequences from one or more environmental samples using a pair of a first primer and a second primer, the first primer designed according to a nucleotide sequence containing a nucleotide 5' half target of a candidate HE obtained in claim 9 and the second primer designed according to a nucleotide sequence containing a nucleotide 3' half target of a candidate HE obtained in claim 9, wherein the environmental samples is chosen based upon one or more habitats from which the candidate HEG or predetermined HEG encoding the candidate HE or predetermined HE was purified, amplified and sequenced; and
(b) cloning the amplified sequences on one or more predetermined vectors.

16. The method according to claim 13 further comprising:
(c) amplification of nucleotide sequences from one or more environmental samples using a pair of a first primer and a second primer, the first primer designed according to a predetermined nucleotide sequence containing a nucleotide 5' half target of a predetermined HE obtained in claim 13 and the second primer designed according to a predetermined nucleotide sequence containing a nucleotide 3' half target of a predetermined HE obtained in claim 13, wherein the environmental samples is chosen based upon one or more habitats from which the candidate HEG or predetermined HEG encoding the candidate HE or predetermined HE was purified, amplified and sequenced; and
(d) cloning the amplified sequences on one or more predetermined vectors.

17. The method according to claim 1 further comprising engineering a final HE capable of cleaving a nucleotide sequence, or a candidate nucleotide target of one or more predetermined HEs, wherein the engineering comprises subjecting a candidate HE or predetermined HE to a process of directed evolution and rational design to generate the final HE capable of cleaving the nucleotide sequence or the candidate nucleotide target of the predetermined HE.

18. The method according to claim 1 wherein any one of the first database, the second database or the third database is a database stored on a storage medium selected from:
   (a) spliced DNA sequences inferred from genomic sequences,
   (b) a database of DNA sequences from one or more organism, and
   (c) a union of (a) and (b).

19. The method according to claim 11 wherein any one of the sixth and the seventh databases is a database stored on a storage medium selected from:
   a) a subset of a human genome database;
   b) a set of sequences comprising genes found in database of disease related genes;
   c) a set of sequences comprising genes found in the database of disease related genes including introns, and flanking regions;
   d) a database stored on a storage medium comprising one or more gene sets of one or more model organisms,
   e) a database stored on a storage medium comprising one or more gene sets of one or more plants;
   f) a database stored on a storage medium comprising one or more gene sets of one or more domesticated animals;
   g) a database stored on a storage medium comprising one or more gene sets of one or more microorganisms used in the biotechnological industry; and
   h) a database stored on a storage medium of genes of human pathogens.

20. The method according to claim 12 wherein any one of the ninth and the eleventh databases is selected from:
   a) a subset of a human genome database;
   b) a set of sequences comprising genes found in a database of disease related genes;
   c) a set of sequences comprising genes found in the database of disease related genes including introns, and flanking regions;

d) a database stored on a storage medium comprising one or more gene sets of one or more model organisms, e) a database stored on a storage medium comprising one or more gene sets of one or more plants;

f) a database stored on a storage medium comprising one or more gene sets of one or more domesticated animals;

g) a database stored on a storage medium comprising one or more gene sets of one or more microorganisms used in the biotechnological industry; and h) a database stored on a storage medium of genes of human pathogens.

21. The method according to claim 13 wherein the first database is a database stored on a storage medium selected from:

a) a subset of a human genome database;

b) a set of sequences comprising genes found in a database of disease related genes;

c) a set of sequences comprising genes found in the database of disease related genes including introns, and flanking regions;

d) a database stored on a storage medium comprising one or more gene sets of one or more model organisms, e) a database stored on a storage medium comprising one or more gene sets of one or more plants;

f) a database stored on a storage medium comprising one or more gene sets of one or more domesticated animals;

g) a database stored on a storage medium comprising one or more gene sets of one or more microorganisms used in the biotechnological industry; and h) a database stored on a storage medium of genes of human pathogens.

22. The method according to claim 14 wherein anyone of the fourth and sixth databases is a database stored on a storage medium selected from:

a) a subset of a human genome database;

b) a set of sequences comprising genes found in a database of disease related genes;

c) a set of sequences comprising genes found in the database of disease related genes including introns, and flanking regions;

d) a database stored on a storage medium comprising one or more gene sets of one or more model organisms, e) a database stored on a storage medium comprising one or more gene sets of one or more plants;

f) a database stored on a storage medium comprising one or more gene sets of one or more domesticated animals;

g) a database stored on a storage medium comprising one or more gene sets of one or more microorganisms used in the biotechnological industry; and h) a database stored on a storage medium of genes of human pathogens.

23. A processor configured to perform the method of claim 1.

* * * * *

SEQUENCE LISTING

<160> NUMBER OF SEQ ID NOS: 10

<210> SEQ ID NO 1
<211> LENGTH: 1362
<212> TYPE: DNA
<213> ORGANISM: Homo sapiens

<400> SEQUENCE: 1

```
tgctttgcca agggtaccaa tgttttaatg gcggatgggt ctattgaatg tattgaaaac      60
attgaggttg gtaataaggt catgggtaaa gatggcagac ctcgtgaggt aattaaattg     120
cccagaggaa gagaaactat gtacagcgtc gtgcagaaaa gtcagcacag agcccacaaa     180
agtgactcaa gtcgtgaagt gccagaatta ctcaagttta cgtgtaatgc gacccatgag     240
ttggttgtta gaacacctcg tagtgtccgc cgtttgtctc gtaccattaa gggtgtcgaa     300
tattttgaag ttattacttt tgagatgggc caaaagaaag cccccgacgg tagaattgtt     360
gagcttgtca aggaagtttc aaagagctac ccaatatctg aggggcctga gagagccaac     420
gaattagtag aatcctatag aaaggcttca aataaagctt attttgagtg gactattgag     480
gccagagatc tttctctgtt gggttcccat gttcgtaaag ctacctacca gacttacgct     540
ccaattcttt atgagaatga ccactttttc gactacatgc aaaaaagtaa gtttcatctc     600
accattgaag gtccaaaagt acttgcttat ttacttggtt tatggattgg tgatggattg     660
tctgacaggg caacttttc ggttgattcc agagatactt ctttgatgga acgtgttact     720
```

-continued

```
gaatatgctg aaaagttgaa tttgtgcgcc gagtataagg acagaaaaga accacaagtt    780
gccaaaactg ttaatttgta ctctaaagtt gtcagaggta atggtattcg caataatctt    840
aatactgaga atccattatg ggacgctatt gttggcttag gattcttgaa ggacggtgtc    900
aaaaatattc cttctttctt gtctacggac aatatcggta ctcgtgaaac atttcttgct    960
ggtctaattg attctgatgg ctatgttact gatgagcatg gtattaaagc aacaataaag   1020
acaattcata cttctgtcag agatggtttg gtttcccttg ctcgttcttt aggcttagta   1080
gtctcggtta acgcagaacc tgctaaggtt gacatgaatg gcaccaaaca taaaattagt   1140
tatgctattt atatgtctgg tggagatgtt ttgcttaacg ttctttcgaa gtgtgccggc   1200
tctaaaaaat tcaggcctgc tcccgccgct gcttttgcac gtgagtgccg cggattttat   1260
ttcgagttac aagaattgaa ggaagacgat tattatggga ttactttatc tgatgattct   1320
gatcatcagt ttttgcttgc caaccaggtt gtcgtccata at                     1362
```

<210> SEQ ID NO 2
<211> LENGTH: 455
<212> TYPE: PRT
<213> ORGANISM: Homo sapiens

<400> SEQUENCE: 2

```
Gly Cys Phe Ala Lys Gly Thr Asn Val Leu Met Ala Asp Gly Ser Ile
1               5                   10                  15

Glu Cys Ile Glu Asn Ile Glu Val Gly Asn Lys Val Met Gly Lys Asp
            20                  25                  30

Gly Arg Pro Arg Glu Val Ile Lys Leu Pro Arg Gly Arg Glu Thr Met
        35                  40                  45

Tyr Ser Val Val Gln Lys Ser Gln His Arg Ala His Lys Ser Asp Ser
    50                  55                  60

Ser Arg Glu Val Pro Glu Leu Leu Lys Phe Thr Cys Asn Ala Thr His
65                  70                  75                  80

Glu Leu Val Val Arg Thr Pro Arg Ser Val Arg Arg Leu Ser Arg Thr
                85                  90                  95

Ile Lys Gly Val Glu Tyr Phe Glu Val Ile Thr Phe Glu Met Gly Gln
            100                 105                 110

Lys Lys Ala Pro Asp Gly Arg Ile Val Glu Leu Val Lys Glu Val Ser
        115                 120                 125

Lys Ser Tyr Pro Ile Ser Glu Gly Pro Glu Arg Ala Asn Glu Leu Val
    130                 135                 140

Glu Ser Tyr Arg Lys Ala Ser Asn Lys Ala Tyr Phe Glu Trp Thr Ile
145                 150                 155                 160

Glu Ala Arg Asp Leu Ser Leu Leu Gly Ser His Val Arg Lys Ala Thr
                165                 170                 175

Tyr Gln Thr Tyr Ala Pro Ile Leu Tyr Glu Asn Asp His Phe Phe Asp
            180                 185                 190

Tyr Met Gln Lys Ser Lys Phe His Leu Thr Ile Glu Gly Pro Lys Val
        195                 200                 205

Leu Ala Tyr Leu Leu Gly Leu Trp Ile Gly Asp Gly Leu Ser Asp Arg
    210                 215                 220

Ala Thr Phe Ser Val Asp Ser Arg Asp Thr Ser Leu Met Glu Arg Val
225                 230                 235                 240

Thr Glu Tyr Ala Glu Lys Leu Asn Leu Cys Ala Glu Tyr Lys Asp Arg
                245                 250                 255

Lys Glu Pro Gln Val Ala Lys Thr Val Asn Leu Tyr Ser Lys Val Val
```

```
                          260                 265                 270
Arg Gly Asn Gly Ile Arg Asn Asn Leu Asn Thr Glu Asn Pro Leu Trp
            275                 280                 285

Asp Ala Ile Val Gly Leu Gly Phe Leu Lys Asp Gly Val Lys Asn Ile
        290                 295                 300

Pro Ser Phe Leu Ser Thr Asp Asn Ile Gly Thr Arg Glu Thr Phe Leu
305                 310                 315                 320

Ala Gly Leu Ile Asp Ser Asp Gly Tyr Val Thr Asp Glu His Gly Ile
            325                 330                 335

Lys Ala Thr Ile Lys Thr Ile His Thr Ser Val Arg Asp Gly Leu Val
        340                 345                 350

Ser Leu Ala Arg Ser Leu Gly Leu Val Val Ser Val Asn Ala Glu Pro
            355                 360                 365

Ala Lys Val Asp Met Asn Gly Thr Lys His Lys Ile Ser Tyr Ala Ile
        370                 375                 380

Tyr Met Ser Gly Gly Asp Val Leu Leu Asn Val Leu Ser Lys Cys Ala
385                 390                 395                 400

Gly Ser Lys Lys Phe Arg Pro Ala Pro Ala Ala Phe Ala Arg Glu
            405                 410                 415

Cys Arg Gly Phe Tyr Phe Glu Leu Gln Glu Leu Lys Glu Asp Asp Tyr
        420                 425                 430

Tyr Gly Ile Thr Leu Ser Asp Asp Ser Asp His Gln Phe Leu Leu Ala
            435                 440                 445

Asn Gln Val Val Val His Asn
        450                 455

<210> SEQ ID NO 3
<211> LENGTH: 39
<212> TYPE: DNA
<213> ORGANISM: Homo sapiens

<400> SEQUENCE: 3
atctatgtcg ggtgcggaga aagaggtaat gaaatggca                          39

<210> SEQ ID NO 4
<211> LENGTH: 39
<212> TYPE: DNA
<213> ORGANISM: Homo sapiens

<400> SEQUENCE: 4
atttacgttg gatgtgggga gagggcaac gagatagcg                           39

<210> SEQ ID NO 5
<211> LENGTH: 39
<212> TYPE: DNA
<213> ORGANISM: Homo sapiens

<400> SEQUENCE: 5
atctatgtcg ggtgcggagg aagaggtaat gaaatggca                          39

<210> SEQ ID NO 6
<211> LENGTH: 1611
<212> TYPE: DNA
<213> ORGANISM: Homo sapiens

<400> SEQUENCE: 6
agcattttac cggaagaatg ggttccacta attaaaaacg gtaaagttaa gatattccgc    60
attggggact tcgttgatgg acttatgaag gcgaaccaag gaaaagtgaa gaaaacgggg   120
```

```
gatacagaag ttttagaagt tgcaggaatt catgcgtttt cctttgacag gaagtccaag    180
aaggcccgtg taatggcagt gaaagccgtg ataagcacc gttattccgg aaatgtttat    240
agaatagtct taaactctgg tagaaaaata acaataacag aagggcatag cctatttgtc    300
tataggaacg gggatctcgt tgaggcaact ggggaggatg tcaaaattgg ggatcttctt    360
gcagttccaa gatcagtaaa cctaccagag aaaagggaac gcttgaatat tgttgaactt    420
cttctgaatc tctcaccgga agagacagaa gatataatac ttacgattcc agttaaaggc    480
agaaagaact tcttcaaggg aatgttgaga acattacgtt ggattttggg tgaggaaaag    540
agagtaagga cagcgagccg ctatctaaga caccttgaaa atctcggata cataaggttg    600
aggaaaattg gatacgacat cattgataag gaggggcttg agaaatatag aacgttgtac    660
gagaaacttg ttgatgttgt ccgctataat ggcaacaaga gagagtattt agttgaattt    720
aatgctgtcc gggacgttat ctcactaatg ccagaggaag aactgaagga atggcgtatt    780
ggaactagaa atggattcag aatgggtacg ttcgtagata ttgatgaaga ttttgccaag    840
cttcttggct actatgtgag cgagggaagt gcgaggaagt ggaagaatca aactggaggt    900
tggagttaca ctgtgagatt gtacaacgag aacgatgaag ttcttgacga catgaacac     960
ttagccaaga agttttttgg gaaagtcaaa cgtggaaaga actatgttga dataccaaag   1020
aaaatggctt atatcatctt tgagagcctt tgtgggactt tggcagaaaa caaagggtt    1080
cctgaggtaa tctttacctc atcaaagggc gttagatggg ccttccttga gggttatttc   1140
atcggcgatg cgatgttca cccaagcaag agggttcgcc tatcaacgaa gagcgagctt   1200
ttagtaaatg gccttgttct cctacttaac tcccttggag tatctgccat taagcttgga   1260
tacgatagcg gagtctacag ggtttatgta aacgaggaac ttaagtttac ggaatacaga   1320
aagaaaaaga atgtatatca ctctcacatt gttccaaagg atattctcaa agaaactttt   1380
ggtaaggtct tccagaaaaa tataagttac aagaaattta gagagcttgt agaaaatgga   1440
aaacttgaca gggagaaagc caaacgcatt gagtggttac ttaacggaga tatagtccta   1500
gatagagtcg tagagattaa gagagagtac tatgatggtt acgtttacga tctaagtgtc   1560
gatgaagatg agaatttcct tgctggcttt ggattcctct atgcacataa t            1611
```

<210> SEQ ID NO 7
<211> LENGTH: 537
<212> TYPE: PRT
<213> ORGANISM: Homo sapiens

<400> SEQUENCE: 7

Ser Ile Leu Pro Glu Glu Trp Val Pro Leu Ile Lys Asn Gly Lys Val
1               5                   10                  15

Lys Ile Phe Arg Ile Gly Asp Phe Val Asp Gly Leu Met Lys Ala Asn
            20                  25                  30

Gln Gly Lys Val Lys Lys Thr Gly Asp Thr Glu Val Leu Glu Val Ala
        35                  40                  45

Gly Ile His Ala Phe Ser Phe Asp Arg Lys Ser Lys Lys Ala Arg Val
    50                  55                  60

Met Ala Val Lys Ala Val Ile Arg His Arg Tyr Ser Gly Asn Val Tyr
65                  70                  75                  80

Arg Ile Val Leu Asn Ser Gly Arg Lys Ile Thr Ile Thr Glu Gly His
                85                  90                  95

Ser Leu Phe Val Tyr Arg Asn Gly Asp Leu Val Glu Ala Thr Gly Glu
            100                 105                 110

Asp Val Lys Ile Gly Asp Leu Leu Ala Val Pro Arg Ser Val Asn Leu

```
                  115                 120                 125
        Pro Glu Lys Arg Glu Arg Leu Asn Ile Val Glu Leu Leu Asn Leu
        130                 135                 140

Ser Pro Glu Glu Thr Glu Asp Ile Ile Leu Thr Ile Pro Val Lys Gly
        145                 150                 155                 160

Arg Lys Asn Phe Phe Lys Gly Met Leu Arg Thr Leu Arg Trp Ile Phe
                        165                 170                 175

Gly Glu Glu Lys Arg Val Arg Thr Ala Ser Arg Tyr Leu Arg His Leu
                    180                 185                 190

Glu Asn Leu Gly Tyr Ile Arg Leu Arg Lys Ile Gly Tyr Asp Ile Ile
                    195                 200                 205

Asp Lys Glu Gly Leu Glu Lys Tyr Arg Thr Leu Tyr Glu Lys Leu Val
        210                 215                 220

Asp Val Val Arg Tyr Asn Gly Asn Lys Arg Glu Tyr Leu Val Glu Phe
        225                 230                 235                 240

Asn Ala Val Arg Asp Val Ile Ser Leu Met Pro Glu Glu Glu Leu Lys
                        245                 250                 255

Glu Trp Arg Ile Gly Thr Arg Asn Gly Phe Arg Met Gly Thr Phe Val
                    260                 265                 270

Asp Ile Asp Glu Asp Phe Ala Lys Leu Leu Gly Tyr Tyr Val Ser Glu
                    275                 280                 285

Gly Ser Ala Arg Lys Trp Lys Asn Gln Thr Gly Gly Trp Ser Tyr Thr
        290                 295                 300

Val Arg Leu Tyr Asn Glu Asn Asp Glu Val Leu Asp Asp Met Glu His
        305                 310                 315                 320

Leu Ala Lys Lys Phe Phe Gly Lys Val Lys Arg Gly Lys Asn Tyr Val
                        325                 330                 335

Glu Ile Pro Lys Lys Met Ala Tyr Ile Ile Phe Glu Ser Leu Cys Gly
                    340                 345                 350

Thr Leu Ala Glu Asn Lys Arg Val Pro Glu Val Ile Phe Thr Ser Ser
                    355                 360                 365

Lys Gly Val Arg Trp Ala Phe Leu Glu Gly Tyr Phe Ile Gly Asp Gly
        370                 375                 380

Asp Val His Pro Ser Lys Arg Val Arg Leu Ser Thr Lys Ser Glu Leu
        385                 390                 395                 400

Leu Val Asn Gly Leu Val Leu Leu Leu Asn Ser Leu Gly Val Ser Ala
                        405                 410                 415

Ile Lys Leu Gly Tyr Asp Ser Gly Val Tyr Arg Val Tyr Val Asn Glu
                    420                 425                 430

Glu Leu Lys Phe Thr Glu Tyr Arg Lys Lys Asn Val Tyr His Ser
                    435                 440                 445

His Ile Val Pro Lys Asp Ile Leu Lys Glu Thr Phe Gly Lys Val Phe
        450                 455                 460

Gln Lys Asn Ile Ser Tyr Lys Lys Phe Arg Glu Leu Val Glu Asn Gly
        465                 470                 475                 480

Lys Leu Asp Arg Glu Lys Ala Lys Arg Ile Glu Trp Leu Leu Asn Gly
                        485                 490                 495

Asp Ile Val Leu Asp Arg Val Val Glu Ile Lys Arg Glu Tyr Tyr Asp
                    500                 505                 510

Gly Tyr Val Tyr Asp Leu Ser Val Asp Glu Asp Glu Asn Phe Leu Ala
                    515                 520                 525

Gly Phe Gly Phe Leu Tyr Ala His Asn
        530                 535
```

```
<210> SEQ ID NO 8
<211> LENGTH: 31
<212> TYPE: DNA
<213> ORGANISM: Homo sapiens

<400> SEQUENCE: 8
tggcaaacag ctattatggg tattatgggt a                              31

<210> SEQ ID NO 9
<211> LENGTH: 31
<212> TYPE: DNA
<213> ORGANISM: Homo sapiens

<400> SEQUENCE: 9
tagcgaatag ttactacgga tactacggat a                              31

<210> SEQ ID NO 10
<211> LENGTH: 31
<212> TYPE: DNA
<213> ORGANISM: Homo sapiens

<400> SEQUENCE: 10
tggcaaacag cgattatggg tattatgggt a                              31
```